(12) United States Patent
Schultz et al.

(10) Patent No.: US 7,943,608 B2
(45) Date of Patent: May 17, 2011

(54) DIAZEPINOES

(75) Inventors: Melanie Schultz, Darmstadt (DE); Lars Thore Burgdorf, Frankfurt am Main (DE); Dirk Finsinger, Darmstadt (DE); Andree Blaukat, Muehltal (DE); Hartmut Greiner, Weiterstadt (DE); Christina Esdar, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 347 days.

(21) Appl. No.: 12/158,333

(22) PCT Filed: Nov. 28, 2006

(86) PCT No.: PCT/EP2006/011411
§ 371 (c)(1),
(2), (4) Date: Jun. 20, 2008

(87) PCT Pub. No.: WO2007/079826
PCT Pub. Date: Jul. 19, 2007

(65) Prior Publication Data
US 2008/0318934 A1    Dec. 25, 2008

(30) Foreign Application Priority Data

Dec. 22, 2005   (DE) .................. 10 2005 061 655

(51) Int. Cl.
*C07D 487/04*   (2006.01)
*A61K 31/5517*  (2006.01)
(52) U.S. Cl. ........................... 514/220; 540/495
(58) Field of Classification Search .............. 540/495; 514/220
See application file for complete search history.

(56) References Cited

U.S. PATENT DOCUMENTS 3,872,122 A   3/1975   Juby et al.
4,311,700 A   1/1982   Schaefer

FOREIGN PATENT DOCUMENTS

WO   WO 81/00568 A1    3/1981
WO   WO 2004/076424 A1 9/2004

OTHER PUBLICATIONS

M. Palanki et al. "Synthesis and Structure-Activity Relationship Studies of Conformationally Restricted Analogs of 2-Chloro-4-Trifluoromethylpyrimidine-5-[N-(3',5'-Bis(Trifluoromethylphenyl)]Carboxamide", Med. Chem. Res., vol. 10, No. 1 (2000) pp. 19-29.
A. Dlugosz et al., "Synthesis and Biological Activity of Pyrimidobenzodiazepine Derivatives. New Ring Systems: Triazolo- and Tetrazolo- Pyrimido-Benzodiazepines", Pharmazie, vol. 50 (1995) pp. 180-182.

*Primary Examiner* — Bruck Kifle
(74) *Attorney, Agent, or Firm* — Millen, White, Zelano & Branigan, P.C.

(57) ABSTRACT

The invention relates to compounds of the formula (I), to the preparation and use thereof for the preparation of a medicament for the treatment of diseases, in particular tumours and/or diseases in the development or course of which kinases are involved.

7 Claims, No Drawings

DIAZEPINOES

The invention relates to compounds of the formula I

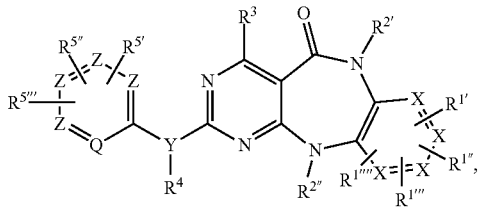

in which $R^{1'}, R^{1''}, R^{1'''}, R^{1''''}, R^3, R^4, R^{5'}, R^{5''}, R^{5'''}$
  each, independently of one another, denote H, A, $R^6$, Ar, $OR^6$, $SR^6$, OAr, SAr, $N(R^6)_2$, NHAr, Hal, $NO_2$, CN, $(CH_2)_mCOOR^6$, $(CH_2)_mCOOAr$, $(CH_2)_mCON(R^6)_2$, $(CH_2)_mCONAAr$, COA, $COR^6$, COAr, $S(O)_mA$, $S(O)_mAr$, NACOA, NACOAr, $NASO_2A$, $NASO_2Ar$, NHCOA, NHCOAr, $NHCON(R^6)_2$, NHCONHA, NHCONHAr, $SO_2N(R^6)_2$, $SO_2NAAr$, $M(CH_2)_nN(R^6)_2$, $M(CH_2)_nNAR^6$, $M(CH_2)_nNA_2$, $M(CH_2)_n(R^6)_n$, $M(CH_2)_n(R^6)_n$, $M(CH_2)_n(R^6)_n$, $M(CH_2)_n(R^6)_n$, $M(CH_2)_n$-oxopiperazine, $M(CH_2)_n$-oxomorpholine, $M(CH_2)_n$-oxopyrrolidine, $M(CH_2)_nC(CH_3)_n(CH_2)_nN(R^6)_2$, $M(CH_2)_nM(R^6)_nSO_mA$, $M(CH_2)_nM(R^6)_nSO_mM(R^6)_n$, $M(CH_2)_nM(R^6)_nSO_mAr$, $(CH_2)_nM(R^6)_nSO_mA$, $(CH_2)_nM(R^6)_nSO_mM(R^6)_n$, $(CH_2)_nM(R^6)_nSO_mAr$, $M(CH_2)_nSO_mA$, $M(CH_2)_nSO_mN(R^6)_nA$, $M(CH_2)_nSO_mAr$, $(CH_2)_nSO_mA$, $(CH_2)_nSO_mM(R^6)_{n7}$ $(CH_2)_nSO_mAr$,
  where two adjacent radicals $R^{1'}, R^{1''}, R^{1'''}$ or $R^{1''''}$ may form a saturated or unsaturated, five- or six-membered carbo- or heterocycle which is optionally mono- or disubstituted by M with one another, $R^{2'}, R^{2''}$ each, independently of one another, denote $R^6$, $R^6$ denotes H, Hal, OH, CN, $NH_2$, $NO_2$, $SO_2$, unbranched or branched alkyl having 1-4 C atoms, in which one $CH_2$ group may be replaced by an O or S atom and/or by an NH, NA, CONH, NHCO or —CH═CH— group and/or, in addition, 1-4H atoms may be replaced by Hal, and in which one $CH_3$ group may be replaced by Hal, OH, CN, $NH_2$, $NHR_7$, $NR^7_2$, $NO_2$ or $SO_2$, where $R^7$=methyl or ethyl, where two radicals $R^6$, together with the atom to which they are linked, may form a saturated or unsaturated five- or six-membered carbo- or heterocycle, n denotes 0, 1, 2, 3, 4 or 5, m denotes 0, 1 or 2, A denotes unbranched, branched or cyclic alkyl having 1-14 C atoms, in which one or two $CH_2$ groups may be replaced by an O or S atom and/or by an NH, CONH, NHCO, CO or —CH═CH— group and/or, in addition, 1-7H atoms may be replaced by Hal, and in which one or two $CH_3$ groups may be replaced by $R^6$, Ar denotes a mono- or bicyclic aromatic homo- or heterocycle having 1 to 4 N, O and/or S atoms and 5 to 10 skeleton atoms, which may be unsubstituted or mono-, di- or trisubstituted by carbonyl oxygen, Hal, A, OH, OA, $NH_2$, NHA, $NA_2$, $NO_2$, ON, OCN, SCN, COOH, COOA, $CONH_2$, CONHA, $CONA_2$, NHCOA, $NHCONH_2$, $NHSO_2A$, CHO, COA, $SO_2NH_2$ and/or $S(O)_mA$, Hal denotes F, Cl, Br or I, X denotes $CR^1$, $CHR^1$, N, $NR^1$, O or S, where at least one X group in each compound of the formula I is $CR^1$ or $CHR^1$ and where furthermore an O or S group is not bonded directly to an N, $NR^1$, O or S group, Y denotes $NR^4$, O or S, Z denotes $CR^5$, $CHR^5$, N, $NR^5$, O or S, where at least two Z groups in each compound of the formula I are $CR^5$ or $CHR^5$ and where furthermore an O or S group is not bonded directly to an N, $NR^5$, O or S group, Q denotes $CR^5$, $CHR^5$, or a bond, M denotes NH, O, S and ----- denotes a single or double bond, and pharmaceutically acceptable salts, derivatives, solvates and stereoisomers thereof, including mixtures thereof in all ratios.

It has been found that the compounds of the formula I are capable of inhibiting, regulating and/or modulating signal transduction mediated by kinases. In particular, the compounds according to the invention are suitable as inhibitors of kinases. Thus, medicaments and pharmaceutical compositions according to the invention can be effectively employed for the treatment of diseases that are caused, mediated and/or propagated by kinases and/or by kinase-mediated signal transduction. Thus, the compounds according to the invention are suitable for the treatment and prophylaxis of cancer, tumour growth, arteriosclerosis, diabetic retinopathy, inflammatory diseases, psoriasis and the like in mammals.

BACKGROUND OF THE INVENTION

Cancer is a disease whose causes are to be seen, inter alia, in disturbed signal transduction. In particular, deregulated signal transduction via kinases plays a central role in the development, growth and spread of cancer (Blume-Jensen, P. and T. Hunter, Nature 411: 355-365, 2001; Hanahan D. and R. A. Weinberg, Cell 100.57-70, 2000). Various receptor kinases and cytoplasmatic kinases and the growth factors binding to them may thus be involved in deregulated apoptosis, tissue invasion, metastasis and generally in signal transduction mechanisms which lead to cancer.

As already mentioned, one of the principal mechanisms by which cellular regulation is effected is the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and frequently influence one another, as is evident from the existence of many protein kinases as well as phosphatases. Phosphorylation of proteins occurs at serine, threonine or tyrosine residues, and protein kinases have therefore been classified in accordance with their specificity of the phosphorylation site in serine/threonine kinases and tyrosine kinases. Since phosphorylation is a very widespread process within cells and since cellular phenotypes are largely influenced by the activity of these pathways, it is currently believed that a large number of conditions and/or diseases are attributable to either aberrant activation or functional mutations in the molecular components of kinase cascades. Consequently, considerable attention has been devoted to the characterisation of these proteins and compounds that are able to modulate their activity (see review article: Weinstein-Oppenheimer et al., Pharma. &. Therap. 88:229-279, 2000). Various possibilities for the inhibition, regulation and modulation of kinases encompass, for example, the provision of antibodies, antisense ribozymes and inhibitors. In oncology research, tyrosine kinases, in particular, have hitherto been regarded as highly promising targets. Thus, numerous synthetic small molecules are undergoing clinical development as tyrosine kinase inhibitors for the treatment of cancer, for example Iressa® or Gleevec®. However, numerous problems, such as side effects, dosage, resistance of the tumour, tumour specificity and patient selection, still have to be solved here.

Serine/threonine kinases are a class of enzymes which catalyse the transfer of the terminal phosphate of adenosine triphosphate to serine or threonine residues in protein substrates. It is thought that serine/threonine kinases, through substrate phosphorylation, play a crucial rote in signal transduction for a number of cellular functions. Although the precise mechanisms of signal transduction are still unclear, it has been shown that serine/threonine kinases, besides tyrosine kinases, are important factors in cell proliferation, carcinogenesis and cell differentiation.

They may therefore be involved in diseases such as cancer, psoriasis and hyperimmune reactions.

The present invention now relates to compounds of the formula I, preferably as regulators, modulators or inhibitors of protein kinases, in particular of the serine/threonine kinase type, which include, inter alia, phosphoinositide-dependent kinase (PDK). The compounds according to the invention are particularly effective in the inhibition of serine/threonine kinase PDK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

Diseases caused by protein kinases, such as PDK1, are characterised by anomalous activity or hyperactivity of such protein kinases. Anomalous activity relates either to: (1) the expression in cells which do not usually express these protein kinases; (2) increased kinase expression which results in undesired cell proliferation, such as cancer; (3) increased kinase activity which results in undesired cell proliferation, such as cancer, and/or in hyperactivity of the corresponding protein kinases. Hyperactivity relates either to amplification of the gene which encodes a certain protein kinase or the generation of an activity level which can be correlated with a cell proliferation disease (i.e. the severity of one or more symptoms of the cell proliferation disease increases with increasing kinase level) the bioavailability of a protein kinase can also be influenced by the presence or absence of a set of binding proteins of this kinase.

In the case of PDK1, anomalous activity of the substrates PKB and S6K of this kinase has been observed in a large number of types of cancer which exhibit point mutation of the PTEN gene, which results in uncontrolled proliferation and an increased survival rate. Inhibitors of PDK1 should therefore prove advantageous in the treatment of cancer cells with constitutively activated AGC kinases.

Inhibitors of PDK1 are disclosed, for example, in WO 04/048343 or WO 05/054238.

The most important types of cancer which can be treated using a compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In additions the compounds according to the invention can be used to achieve additive or synergistic effects in certain existing cancer chemotherapies and radiotherapies and/or to restore the efficacy of certain existing cancer chemotherapies and radiotherapies.

A series of diazepinones have been described as kinase inhibitors in WO 04/076424.

The invention was now based on the object of finding further diazepinones having advantageous therapeutic properties which can be used for the preparation of medicaments.

DESCRIPTION OF THE INVENTION

It has been found that the compounds of the formula I and salts thereof have very valuable pharmacological properties while being well tolerated. In particular, it has been found that the compounds of the formula I according to the invention surprisingly are effective kinase inhibitors, exhibiting, in particular, a serine/threonine kinase-inhibiting action and particularly an PDK1-inhibiting action.

In general, all radicals which occur more than once may be identical or different, i.e. are independent of one another. Above and below, the radicals and parameters have the meanings indicated for the formula I, unless expressly indicated otherwise.

Accordingly, the invention relates, in particular, to the compounds of the formula I in which at least one of the said radicals has one of the preferred meanings indicated below.

Hal denotes fluorine, chlorine, bromine or iodine, in particular fluorine or chlorine.

A denotes alkyl, is unbranched (linear), branched or cyclic, and has 1, 2, 3, 4, 5, 6, 7, 8, 9, 10, 11, 12, 13 or 14 C atoms.

Thus, A denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl.

A preferably denotes alkyl having 1, 2, 3, 4, 5 or 6 C atoms, in which one or two $CH_2$ groups may be replaced by O or S atoms and/or by NH, NA, CONH, NHCO or —CH=CH- groups and/or in addition 1-7H atoms may be replaced by F and/or Cl, such as, for example, methyl, ethyl, propyl, isopropyl, butyl, isobutyl, sec-butyl, tert-butyl, pentyl, hexyl, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy, and in which one or two $CH_3$ groups may be replaced by $NH_2$, NAH, $NA_2$ or CN, such as, for example, N,N'-dimethylaminoalkyl or cyanoalkyl.

Cycloalkyl or cyclic alkyl preferably denotes cyclopropyl, cyclobutyl, cyclopentyl, cyclohexyl or cycloheptyl.

Ar denotes, for example, unsubstituted phenyl, naphthyl or biphenyl, furthermore preferably, for example, phenyl, naphthyl or biphenyl, each of which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

Ar furthermore denotes phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore denotes 2- or 3-furyl, 2- or 3-thienyl, 1-, 2- or 3-pyrrolyl, 1-2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazoyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6, -or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, 5- or 6-quinoxalinyl, 4-, 5-, or 6-phthalazinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl, each of which is unsubstituted or mono-, di- or trisubstituted, for example, by carbonyl oxygen, F, Cl, Br, methyl, ethyl, propyl, phenyl, benzyl, —CH$_2$-cyclohexyl, hydroxyl, methoxy, ethoxy, amino, methylamino, dimethylamino, nitro, cyano, carboxyl, methoxycarbonyl, aminocarbonyl, methylaminocarbonyl, dimethylaminocarbonyl, acetamino, ureido, methylsulfonylamino, formyl, acetyl, aminosulfonyl and/or methylsulfonyl.

The heterocyclic radicals may also be partially or fully hydrogenated and also denote, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 2-, 3-, 5- or 6-piperidin-1 or 4-yl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

The term "substituted" preferably relates to the substitution by the above-mentioned substituents, where a plurality of different degrees of substitution are possible, unless indicated otherwise.

All physiologically acceptable salts, derivatives, solvates and stereoisomers of these compounds, including mixtures thereof in all ratios, are also in accordance with the invention.

The compounds of the formula I may have one or more centres of chirality. They may accordingly occur in various enantiomeric forms and be in racemic or optically active form. The invention therefore also relates to the optically active forms (stereoisomers), the enantiomers, the racemates, the diastereomers and hydrates and solvates of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

A preferred group of compounds of the formula I conforms to the formula AII

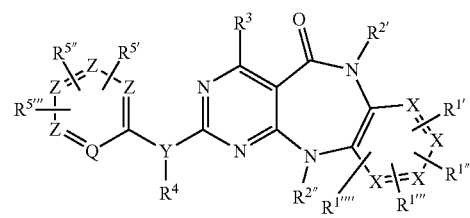

in which $R^{1'}$, $R^{1''}$, $R^{1'''}$, $R^{1''''}$, $R^{2'}$, $R^{2''}$, $R^4$, $R^{5'}$, $R^{5'''}$, $R^{5''''}$, $R^6$, Q, X, Y and Z have the meaning indicated for the formula I, and pharmaceutically acceptable salts, derivatives, solvates and stereoisomers thereof, including mixtures thereof in all ratios.

A further preferred group of compounds of the formula I conforms to the formula AIII

AIII in which $R^{1'}$, $R^{1''}$, $R^{1'''}$, $R^{1''''}$, $R^{2'}$, $R^{2''}$, $R^3$, $R^4$, $R^{5'}$, $R^{5''}$, $R^{5'''}$, $R^6$, X, Y and Z have the meaning indicated for the formula I and pharmaceutically acceptable salts, derivatives, solvates and stereoisomers thereof, including mixtures thereof in all ratios.

A further preferred group of compounds of the formula I conforms to the formula AIV

AIV in which $R^{1'}$, $R^{1''}$, $R^{1'''}$, $R^{1''''}$, $R^{2'}$, $R^{2''}$, $R^3$, $R^4$, $R^{5'}$, $R^{5''}$, $R^{5'''}$, $R^6$, X, Y and Z have the meaning indicated for the formula I, and the pharmaceutically acceptable salts, derivatives, solvates and stereoisomers thereof, including mixtures thereof in all ratios.

A further preferred group of compounds of the formula I conforms to the formula AV

AV in which $R^{1'}$, $R^{1''}$, $R^{1'''}$, $R^{1''''}$, $R^{2'}$, $R^{2''}$, $R^3$, $R^4$, $R^{5'}$, $R^{5''}$, $R^{5'''}$, $R^6$, X, Y and Z have the meaning indicated for the formula I, and the pharmaceutically acceptable salts, derivatives, solvates and stereoisomers thereof, including mixtures thereof in all ratios.

The term $R^1$ is used below as representative of one of the radicals $R^{1'}$, $R^{1''}$, $R^{1'''}$ or $R^{1''''}$, and the term $R^2$ is used below as representative of one of the radicals $R^{2'}$ or $R^{2''}$.

Further preferred sub-groups of compounds of the formula I, AII and AIII, AIV and AV can be expressed by the following sub-formulae Aa to Ah, which conform to the formulae I, AII, AIII, AIV or AV, but in which in the sub-formula Aa
X denotes $CR^1$ or $CHR^1$
and all other radicals have the meaning indicated for the formula I, in the sub-formula Ab
one of the radicals X denotes N or $NR^1$,
the other three radicals X denote $CR^1$ or $CHR^1$
and all other radicals have the meaning indicated for the formula I, in the sub-formula Ac
$R^{5'}$ denotes methyl
and all other radicals have the meaning indicated for the formula I, in the sub-formula Ad
$R^3$ denotes H
and all other radicals have the meaning indicated for the formula I, in the sub-formula Ae
$R^{2'}$, $R^{2''}$ denote H
and all other radicals have the meaning indicated for the formula I, in the sub-formula Af
Y denotes $NR^4$,
$R^4$ denotes H or methyl
and all other radicals have the meaning indicated for the formula I, in the sub-formula Ag
$R^{1'}$, $R^{1''}$ is H,
$R^{1'''}$ is H, Hat or methyl,
$R^{1''''}$ is H, Hal, methyl, ethyl, n-propyl, 2-propyl, butyl, isobutyl, sec-butyl tert-butyl, methoxy, $CHal_3$, $CF_3$, OH, $OCH_2CH_2OH$, $SCH_2CH_3$, $NHCH_3$, $N(CH_3)_2$, CN, COOH, $COOCH_3$, $SO_2OH$, $OCHal_3$, $OCF_3$, NHCOA, NHCOAr, $NHCON(R^6)_2$, NHCONHA, NHCONHAr, where A and $R^6$ are H, cyclopentyl, cyclohexyl, n-propyl, 2-propyl, ethyl, sec-butyl or tert-butyl and Ar is thiophen-2 or 3-yl, 3,5-demimethylisoxazol-4-yl, and two radicals $R^6$, together with the amide nitrogen atom, may form a tetrahydropyrrole ring,
and all other radicals have the meaning indicated for the formula I, in the sub-formula Ah
one of the radicals X is N or $NR^1$,
the other three radicals X is $CR^1$ or $CHR^1$,
Y is $R^4$,
$R^4$ is H or methyl,
$R^{5'}$ is methyl,
$R^{2'}$, $R^{2''}$, $R^3$ are H,
$R^{1'}$, $R^{1''}$ are H,
$R^{1'''}$ is H, Hal or methyl,
$R^{1''''}$ is H, Hal, methyl, ethyl, n-propyl, 2-propyl, butyl, isobutyl, sec-butyl tert-butyl, methoxy, $CHal_3$, $CF_3$, OH, $OCH_2CH_2OH$, $SCH_2CH_3$, $NHCH_3$, $N(CH_3)_2$, CN, COOH, $COOCH_3$, $SO_2OH$, $OCHal_3$, $OCF_3$, NHCOA, NHCOAr, $NHCON(R^6)_2$, NHCONHA, NHCONHAr, where A and $R^6$ are H, cyclopentyl, cyclohexyl, n-propyl, 2-propyl, ethyl, sec-butyl or tert-butyl and Ar is thiophen-2 or 3-yl, 3,5-demimethylisoxazol-4-yl, and two radicals $R^6$, together with the amide nitrogen atom, may form a tetrahydropyrrole ring,
and all other radicals have the meaning indicated for the formula I
and pharmaceutically acceptable salts, derivatives, solvates and stereoisomers thereof, including mixtures thereof in all ratios.

Particular preference is given to compounds selected from the compounds shown in Table 1 and pharmaceutically acceptable salts, derivatives, solvates and stereoisomers thereof, including mixtures thereof in all ratios.

TABLE 1

| | | IC50 PDK1 (µM) | HPLC (min) (1) | HPLC-MS (min m/e) | Product |
|---|---|---|---|---|---|
| 1 | (structure) | 2.3 | 1.95 | 0.420 339.2 | orange-brown solid |
| 2 | (structure) | 2.4 | 1.92 | 1.273 353.2 | orange-brown solid |
| 3 | (structure) | 1.0 | 2.06 | 1.387 367.2 | orange-brown solid |
| 4 | (structure) | 1.4 | 2.08 | 0.678 373.0 | orange-brown solid |
| 5 | (structure) | 0.8 | 2.01 | 1.229 369.2 | orange-brown solid |
| 6 | (structure) | 1.1 | 2.02 | 1.275 353.2 | orange-brown solid |
| 7 | (structure) | 3.1 | 2.01 | 0.458 355.2 | orange-brown solid |

| # | Structure | | | | |
|---|---|---|---|---|---|
| 8 | (1-methylpiperidin-4-yl)amino pyrimido-benzodiazepinone with 7,8-dimethyl | 2.5 | 1.96 | 1.338 353.2 | orange-brown solid |
| 9 | (1-methylpiperidin-4-yl)amino pyrimido-benzodiazepinone with methyl | 4.8 | 1.96 | 1.253 339.2 | orange-brown solid |
| 10 | N-methyl-N-(1-methylpiperidin-4-yl)amino pyrimido-benzodiazepinone with Cl | 1.7 | 2.04 | 1.380 373.2 | orange-brown solid |
| 11 | (1-methylpiperidin-4-yl)amino pyrimido-benzodiazepinone with CF₃ | 3.9 | 2.07 | 1.372 393.1 | orange-brown solid |
| 12 | (1-methylpiperidin-4-yl)amino pyrimido-benzodiazepinone with methyl | 0.9 | 1.93 | 1.264 339.2 | orange-brown solid |
| 13 | N-methyl-N-(1-methylpiperidin-4-yl)amino pyrimido-benzodiazepinone with Br | 1.7 | 2.05 | 1.427 417.0 | orange-brown solid |
| 14 | N-methyl-N-(1-methylpiperidin-4-yl)amino pyrimido-benzodiazepinone with methyl | 0.4 | 3.25 | 1.320 352.2 | yellow-green solid |

TABLE 1-continued

| | | | | | |
|---|---|---|---|---|---|
| 15 | (structure) | 0.9 | 3.21 | 1.350 383.2 | yellow solid |
| 16 | (structure) | 0.4 | 4.19 | 1.580 395.2 | yellow solid |
| 17 | (structure) | 1.6 | 3.87 | 1.510 407.2 | yellow solid |
| 18 | (structure) | 0.7 | 4.08 | 1.550 381.2 | yellow solid |
| 19 | (structure) | 0.6 | 3.17 | 1.310 339.2 | yellow solid |
| 20 | (structure) | 2.8 | 1.95 | 1.308 367.2 | orange-brown solid |
| 21 | (structure) | 1.0 | 3.16 | 1.330 369.2 | yellow solid |

TABLE 1-continued

| # | Structure | | | | |
|---|---|---|---|---|---|
| 22 | (structure) | 2.6 | 3.34 | 1.410 367.2 | yellow solid |
| 23 | (structure) | 3.6 | 3.15 | 1.350 353.2 | yellow solid |
| 24 | (structure) | | 3.23 | 1.320 353.2 | yellow solid |
| 25 | (structure) | 1.0 | 2.17 | 1.569 421.2 | orange solid |
| 26 | (structure) | 6.2 | 1.99 | 1.346 381.2 | orange solid |
| 27 | (structure) | | 2.96 | 1.260 343.2 | yellow solid |
| 28 | (structure) | | 3.07 | 1.270 357.2 | yellow solid |

TABLE 1-continued
| | Structure | IC50 PDK1 (M) | HPLC (min) (2) | MS (min m/e) | Product |
|---|---|---|---|---|---|
| 29 | 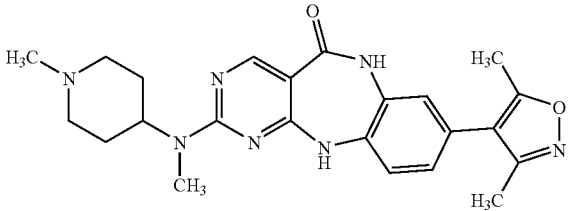 | 3.2 | 2.05 | 1.399 434.2 | orange solid |
| 30 | 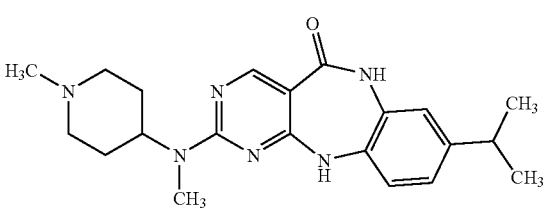 |  | 3.6 | 1.480 381.2 | yellow solid |
| 31 | 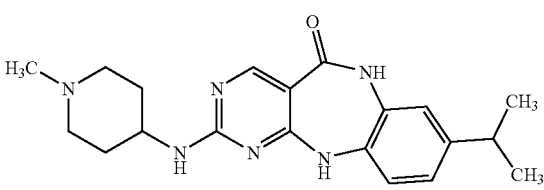 |  | 3.55 | 1.500 367.2 | yellow solid |
| | Structure | IC50 PDK1 (M) | HPLC (min) (2) | MS (min m/e) | Product |
|---|---|---|---|---|---|
| 32 | 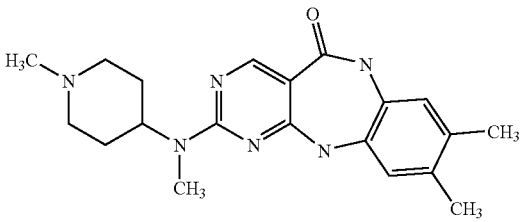 | 6.4E−07 | 3.14 | 366.47 | beige powder |
| 33 | 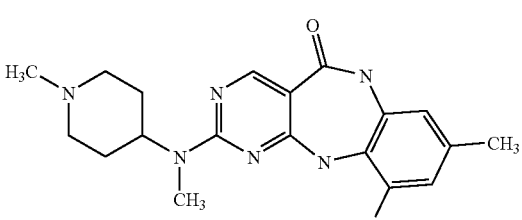 | 1.3E−06 | 3.35 | 366.47 | yellow, solid |
| 34 | 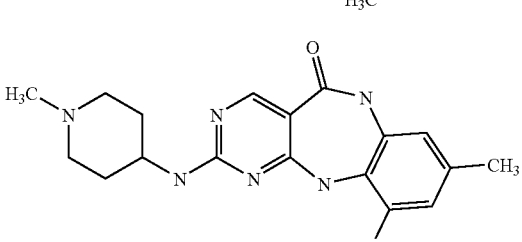 | 3.7E−06 | 3.17 | 352.44 | yellow, solid |
| 35 | 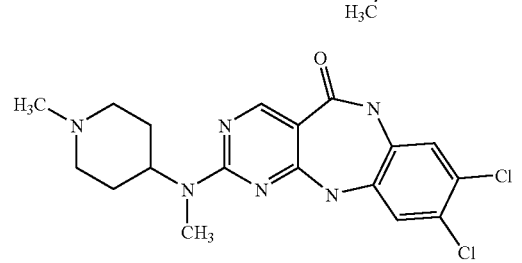 | 3.7E−06 | 3.79 | 407.3 | yellow, solid |

TABLE 1-continued

| # | Structure | IC50 | LogP | MW | Appearance |
|---|---|---|---|---|---|
| 36 | 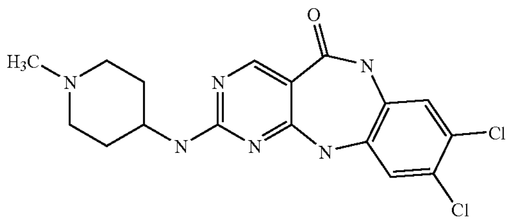 | 1.2E−06 | 3.61 | 393.28 | yellow, solid |
| 37 | 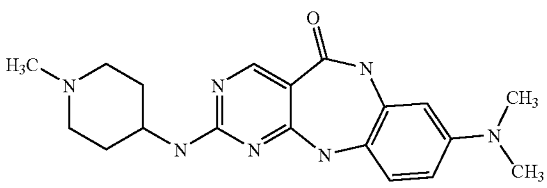 | 1.9E−07 | 2.53 | 367.46 | yellow, flaky |
| 38 | 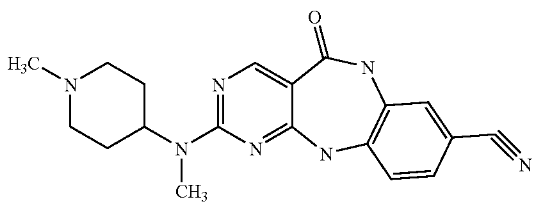 | 6.0E−07 | 3.2 | 363.42 | yellow, flaky |
| 39 | 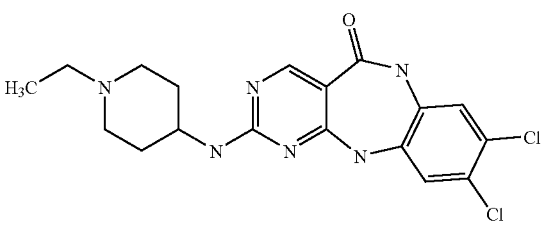 | 4.9E−06 | 3.74 | 407.3 | pale yellow, solid |
| 40 | 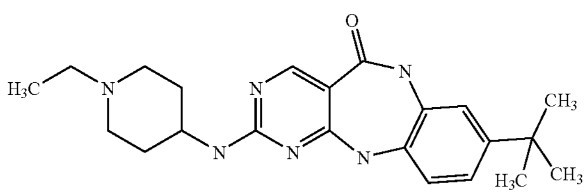 | 1.4E−06 | 4.19 | 394.52 | yellow, flaky |
| 41 | 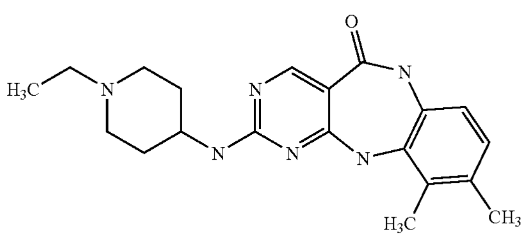 | 6.3E−06 | 3.17 | 366.47 | yellow, solid |
| 42 | 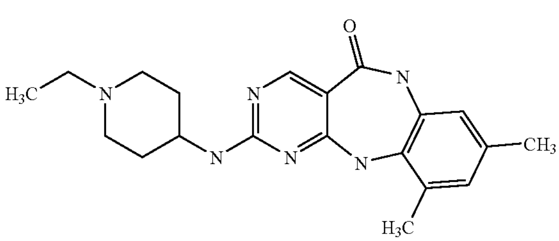 | 4.8E−06 | 3.21 | 366.47 | yellow, solid |

… TABLE 1-continued
| | | | | | |
|---|---|---|---|---|---|
| 43 | 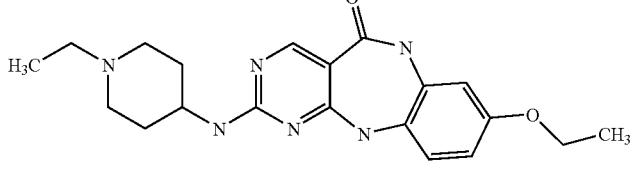 | 2.0E−06 | 3.13 | 382.47 | yellow, solid |
| 44 | 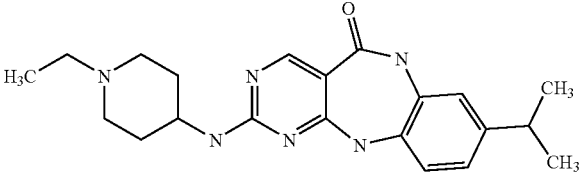 | 9.2E−07 | 3.56 | 380.5 | yellow, solid |
| 45 | 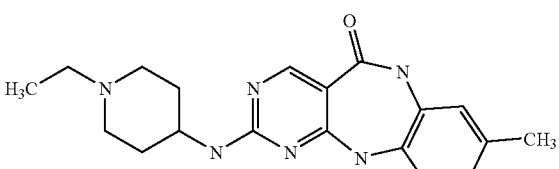 | 1.5E−06 | 3.33 | 352.44 | yellow, flaky |
| 46 | 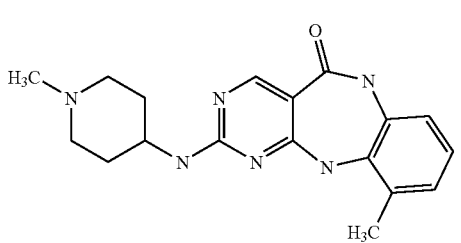 | 2.4E−06 | 3.07 | 338.41 | yellow, flaky |
| 47 | 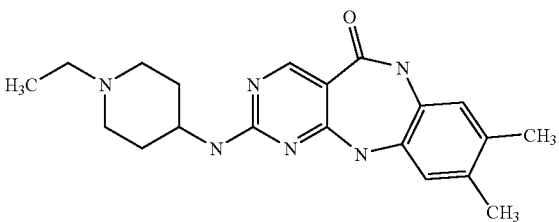 | 1.5E−06 | 3.6 | 366.47 | yellow, flaky |
| 48 | 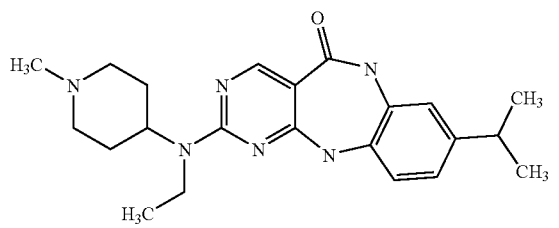 | 3.0E−06 | 3.66 | 394.52 | yellow, solid |
| 49 | 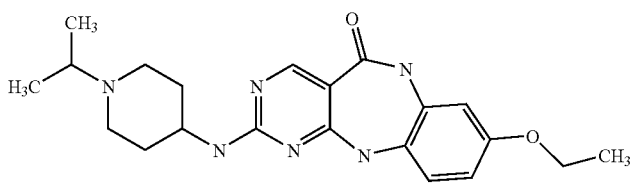 | 5.1E−06 | 3.34 | 396.49 | yellow, solid |

TABLE 1-continued
| | | | | | |
|---|---|---|---|---|---|
| 50 | 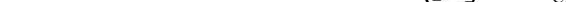 | 1.2E−06 | 3.8 | 394.52 | yellow, solid |
| 51 | 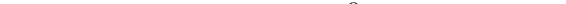 | 2.7E−06 | 4.2 | 408.55 | yellow, flaky |
| 52 | 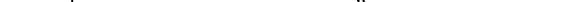 | 3.6E−06 | 3.04/ 3.11* | 370.43 | yellow, flaky |
| 53 | 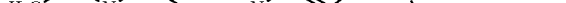 | 2.4E−06 | 3.36 | 366.47 | yellow, flaky |
| 54 |  | 7.1E−06 | 3.17 | 352.44 | yellow, flaky |
| 55 | 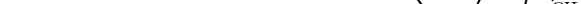 | 2.3E−06 | 2.68/ 2.77* | 363.42 | yellow, flaky |
| 56 | 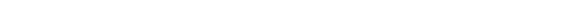 | 1.5E−06 | 2.59/ 2.69* | 349.4 | yellow, flaky |
| 57 | 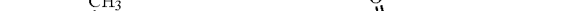 | 2.0E−06 | 3.48 | 380.5 | yellow, flaky |

TABLE 1-continued

| # | Structure | | | | |
|---|---|---|---|---|---|
| 58 | (structure) | 7.1E−06 | 2.82/ 2.90* | 377.45 | yellow, flaky |
| 59 | (structure) | 2.4E−06 | 2.74/ 2.83* | 370.43 | yellow, flaky |
| 60 | (structure) | 2.9E−06 | 3.41 | 406.41 | yellow, flaky |
| 61 | (structure) | 6.5E−06 | 3.61 | 420.44 | yellow, flaky |
| 62 | (structure) | 1.8E−06 | 3.49 | 392.38 | yellow, flaky |
| 63 | (structure) | 1.0E−06 | 3.91 | 420.54 | yellow, solid |
| 64 | (structure) | 4.3E−07 | 3.11 | 382.47 | yellow, solid |
| 65 | (structure) | 5.2E−07 | 3.1 | 369.44 | yellow, solid |

TABLE 1-continued
| | | | | | |
|---|---|---|---|---|---|
| 66 | 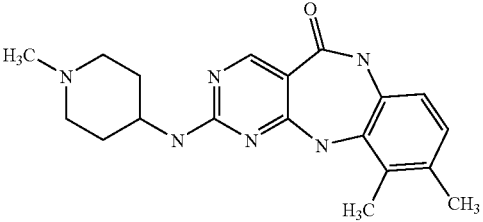 | 3.4E−06 | 3.19/ 3.28* | 352.44 | beige powder |
| 67 | 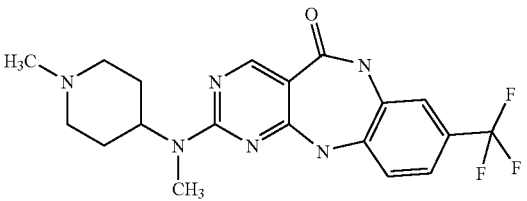 | 1.3E−06 | 3.79 | 406.41 | yellow powder |
| 68 | 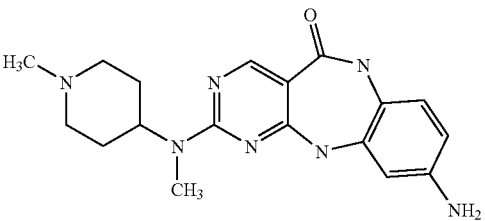 | 5.1E−07 | 2.16 | 353.43 | pale yellow, solid |
| 69 | 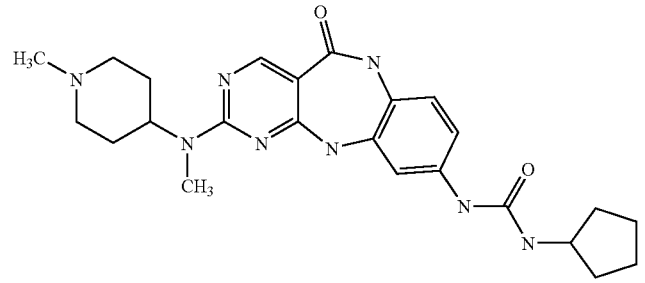 | 6.5E−07 | 3.55 | 464.57 | yellow, solid |
| 70 | 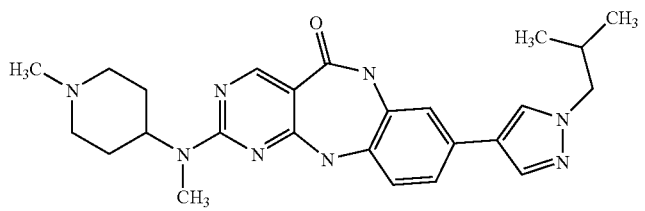 | 1.1E−07 | 3.68 | 460.59 | yellow, solid |
| 71 | 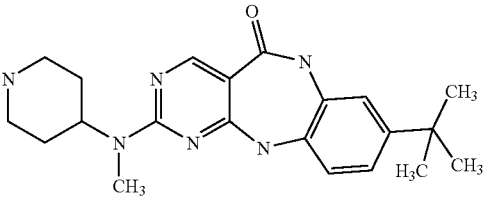 | 4.3E−07 | 4.07 | 380.5 | yellow, flaky |
| 72 | 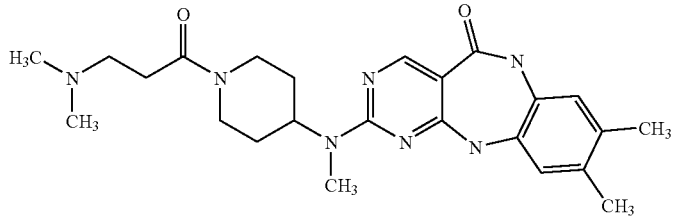 | 8.1E−06 | 3.56/ 3.60* | 451.57 | yellow, flaky |

TABLE 1-continued

| # | Structure | | | | |
|---|---|---|---|---|---|
| 73 | 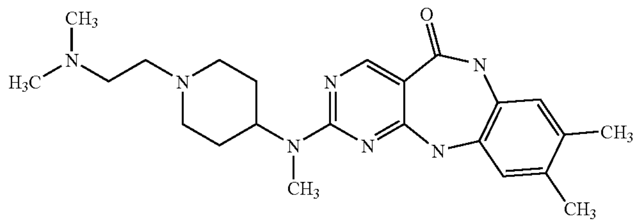 | 3.9E−06 | 3.26/ 3.32* | 423.56 | yellow, flaky |
| 74 | 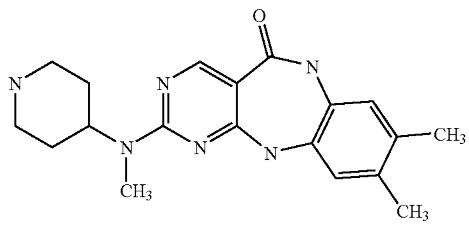 | 3.2E−07 | 3.34/ 3.38* | 352.44 | beige powder |
| 75 | 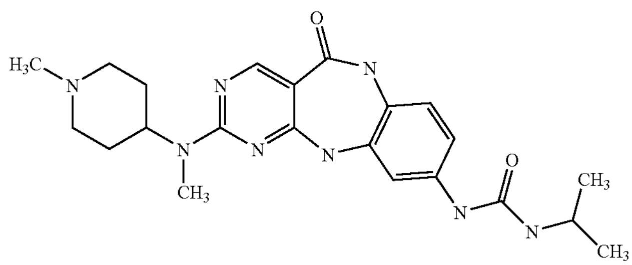 | 9.6E−07 | 3.17 | 438.54 | pale yellow, solid |
| 76 | 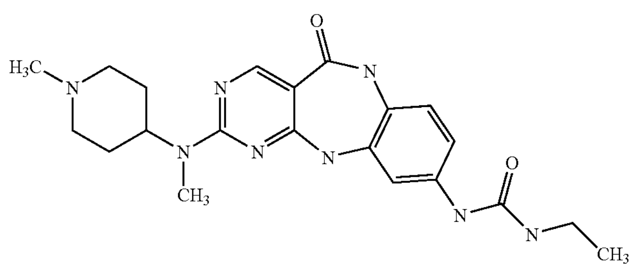 | 1.3E−06 | 2.99 | 424.51 | yellow, solid |
| 77 | 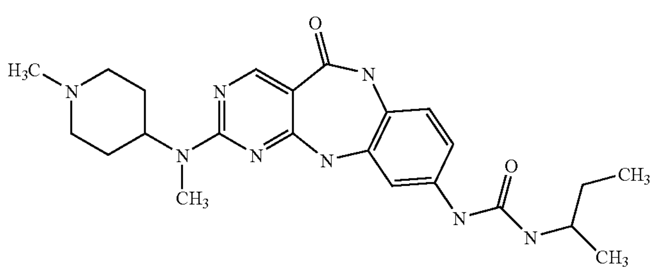 | 9.4E−07 | 3.41 | 452.56 | yellow, solid |
| 78 | 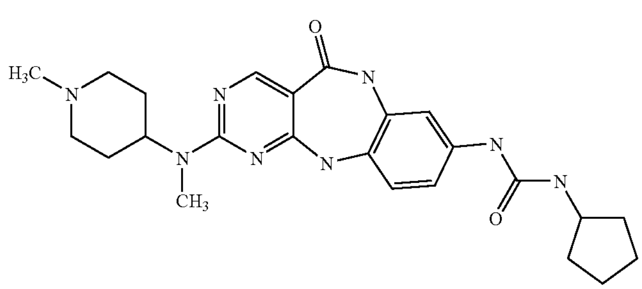 | 1.5E−07 | 3.57 | 464.57 | yellow, solid |

TABLE 1-continued
| | | | | | |
|---|---|---|---|---|---|
| 79 | 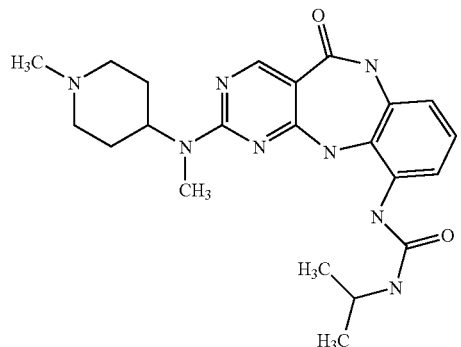 | 6.0E−06 | 2.88 | 438.54 | pale yellow, solid |
| 80 | 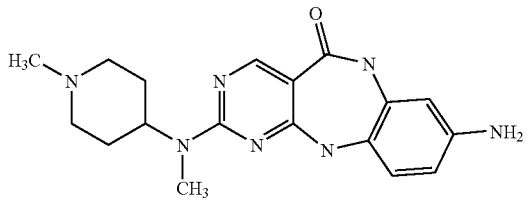 | 1.9E−07 | 2.16 | 353.43 | yellow, solid |
| 81 | 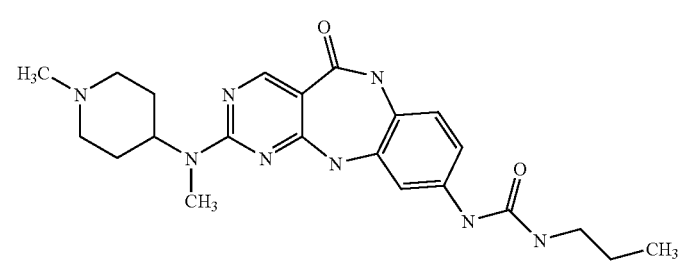 | 4.2E−07 | 3.23 | 438.54 | yellow, solid |
| 82 | 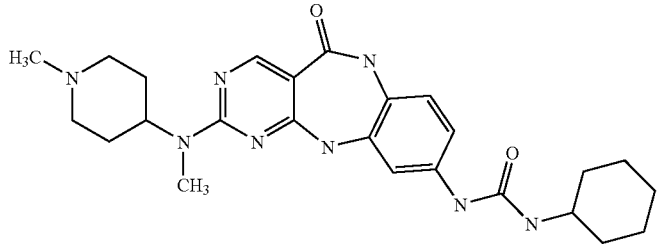 | 7.5E−07 | 3.84 | 478.6 | pale yellow, solid |
| 83 | 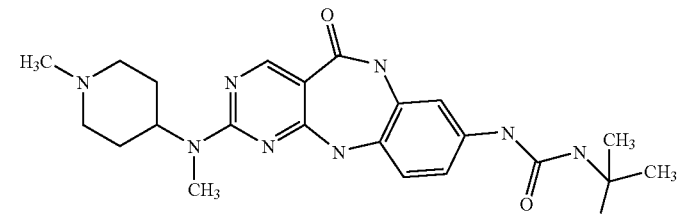 | 2.0E−07 | 3.52 | 452.56 | yellow, solid |

TABLE 1-continued
| | | | | | |
|---|---|---|---|---|---|
| 84 | 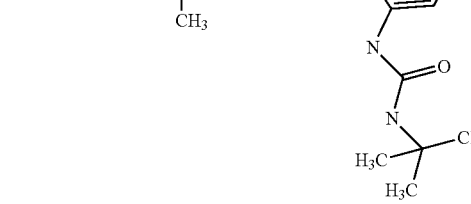 | 5.5E−06 | 3.25 | 452.56 | yellow, solid |
| 85 | 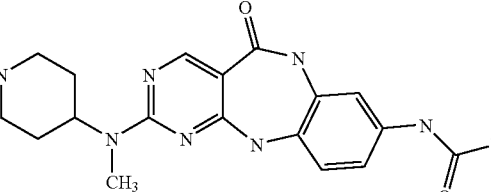 | 2.8E−07 | 2.99 | 424.51 | yellow, solid |
| 86 | 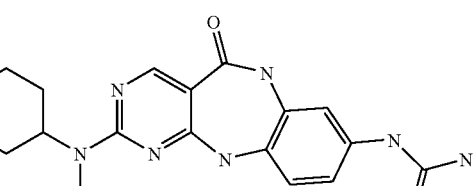 | 2.8E−07 | 3.23 | 438.54 | yellow, solid |
| 87 | 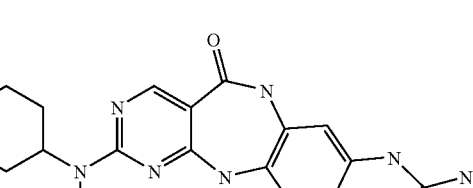 | 2.3E−07 | 3.57 | 452.56 | yellow, solid |
| 88 | 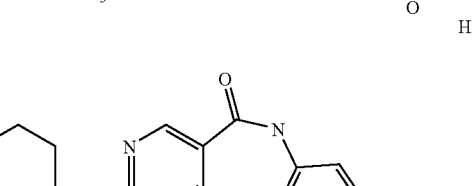 | 1.5E−07 | 3.84 | 478.6 | yellow, solid |
| 89 | 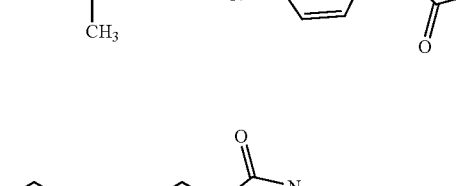 | 2.0E−07 | 3.63 | 478.58 | yellow, solid |

TABLE 1-continued

| | | | | |
|---|---|---|---|---|
| 90 | [structure] | 2.9E−07 | 3.63 | 478.58 | yellow, solid |
| 91 | [structure] | | 2.91 | 438.53 | yellow, solid |
| 92 | [structure] | 7.8E−06 | 3.17 | 452.56 | pale yellow, solid |
| 93 | [structure] | 3.5E−06 | 3.57 | 478.6 | pale yellow, solid |

TABLE 1-continued

| # | Structure | IC50 | logP | MW | Appearance |
|---|-----------|------|------|-----|------------|
| 94 | 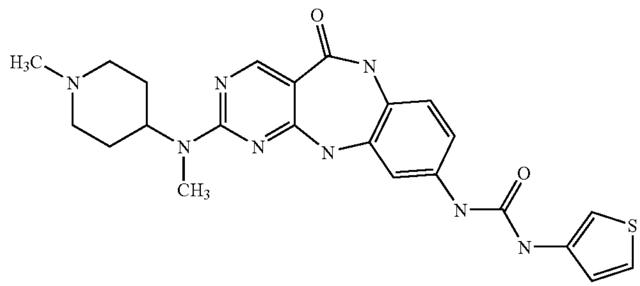 | 1.6E−07 | 3.65 | 478.58 | pale yellow, solid |
| 95 | 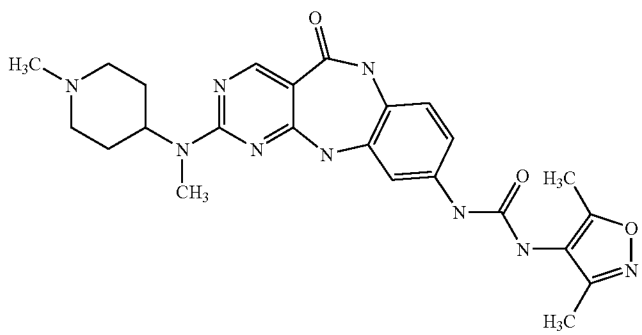 | 9.5E−07 | 3.15 | 491.55 | pale yellow, solid |
| 96 | 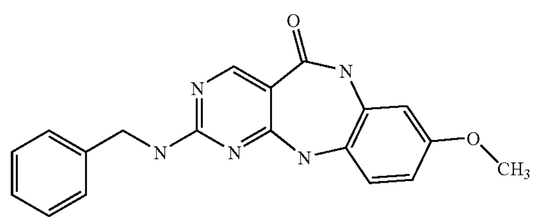 | | 4.49 | 347.38 | beige, flaky |
| 97 | 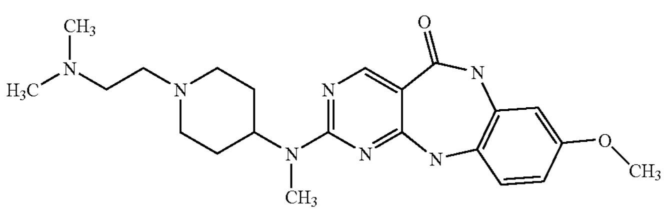 | | 3.96 | 425.53 | yellow, flaky |
| 98 | 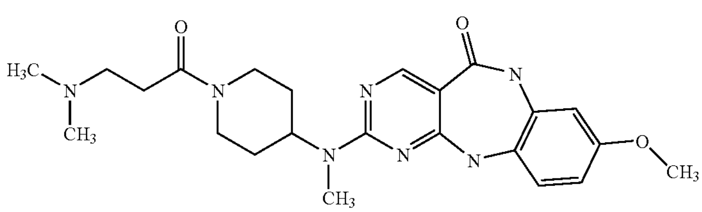 | | 3.13/ 3.20* | 453.54 | yellow, flaky |
| 99 | 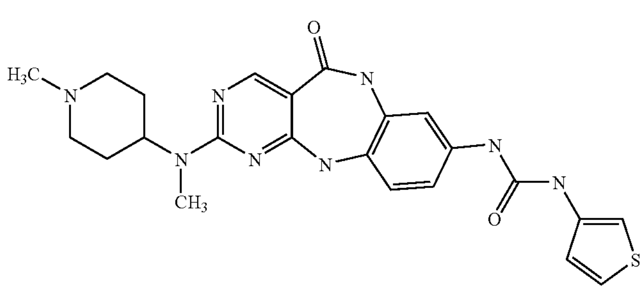 | 1.2E−07 | 3.65 | 478.58 | yellow, solid |

TABLE 1-continued

| # | Structure | IC50 | logP | MW | Appearance |
|---|---|---|---|---|---|
| 100 | 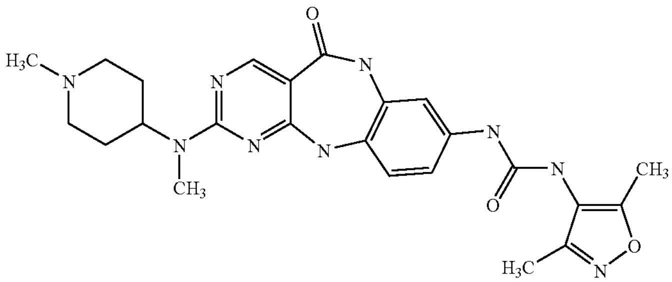 | 2.2E−07 | 3.12 | 491.55 | yellow, solid |
| 101 | 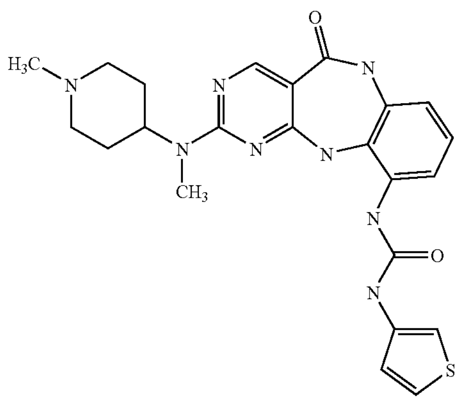 | 3.4E−07 | 3.2 | 478.58 | pale yellow, solid |
| 102 | 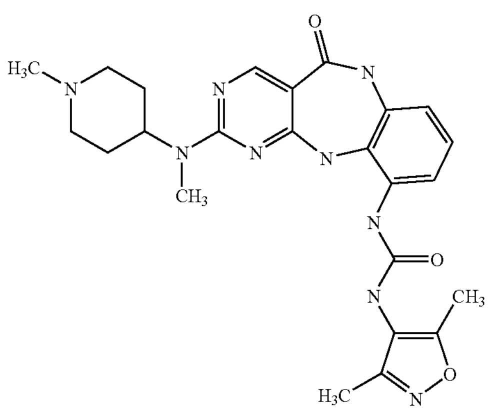 | 3.4E−06 | 2.91 | 491.55 | pale yellow, solid |
| 103 | 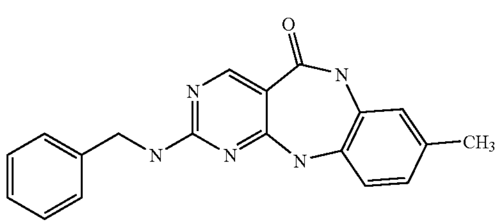 | | 4.62 | 331.38 | yellow, flaky |
| 104 | 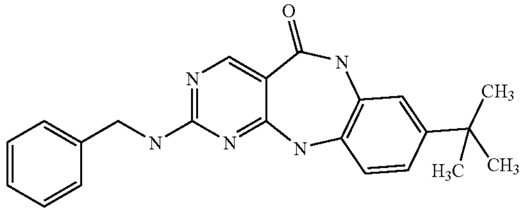 | | 5.54 | 373.46 | yellow, flaky |

TABLE 1-continued

| # | Structure | | | |
|---|---|---|---|---|
| 105 | 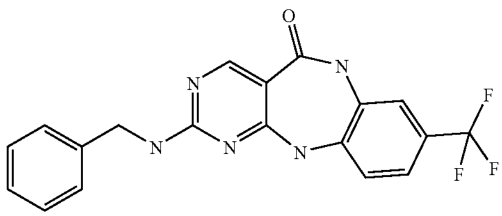 | 5.18 | 385.35 | yellow, flaky |
| 106 | 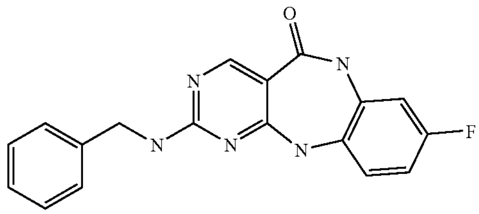 | 4.44 | 335.34 | yellow, flaky |
| 107 | 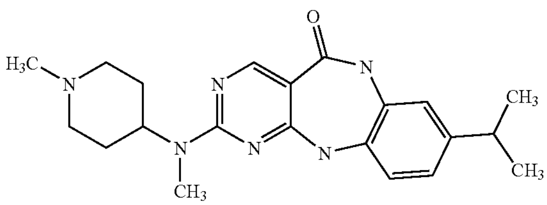 | 3.67 | 380.49 | pale yellow, solid |
| 108 | 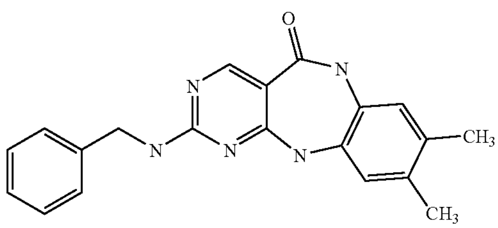 | 2.96 | 345.4 | beige powder |
| 109 | 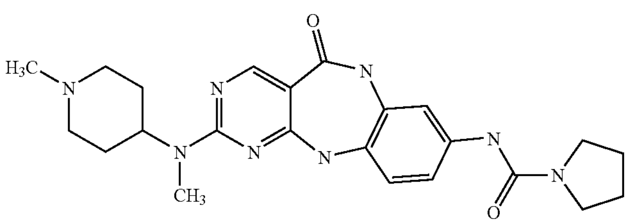 | 3.23 | 450.54 | yellow, solid |
| 110 | 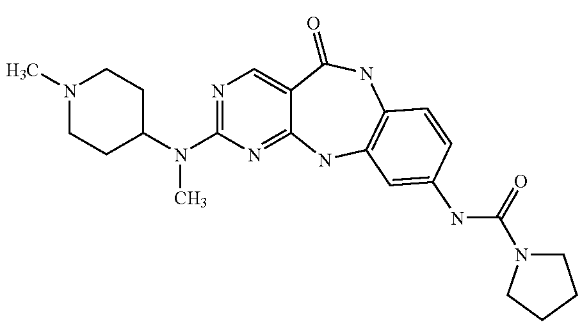 | 3.23 | 450.54 | yellow, solid |

TABLE 1-continued
| | | | | |
|---|---|---|---|---|
| 111 | 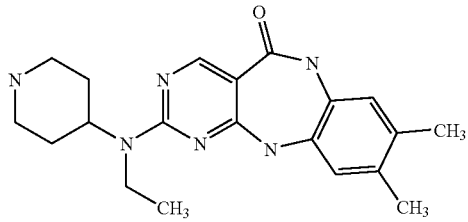 | 3.51 | 366.47 | yellow, flaky |
| 112 | 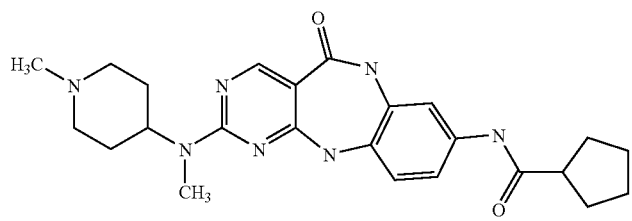 | 3.6 | 449.56 | yellow, solid |
| 113 | 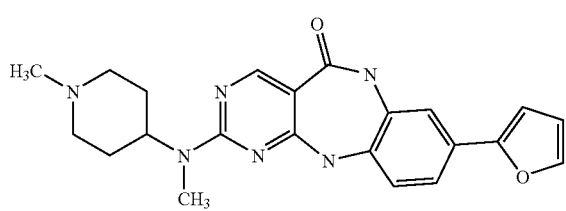 | 3.73 | 404.47 | yellow, solid |
| 114 | 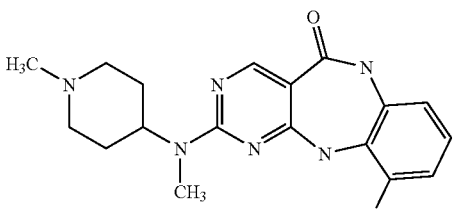 | 2.61 | 353.43 | pale yellow, solid |
| 115 | 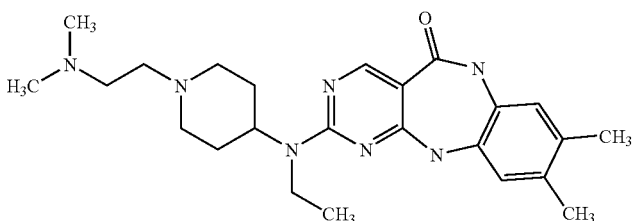 | 3.4 | 437.59 | yellow, flaky |
| 116 | 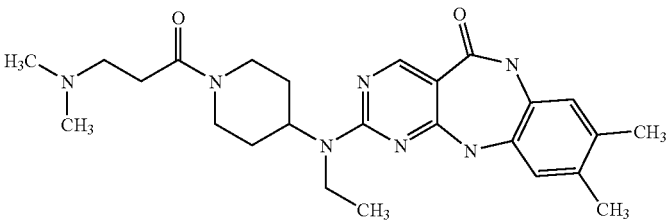 | 3.75 | 465.6 | yellow, solid |
| 117 | 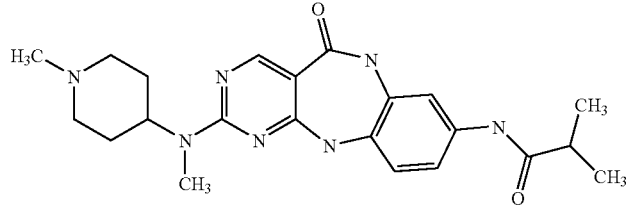 | 3.17 | 423.52 | yellow, solid |

TABLE 1-continued

| # | Structure | RT | MW | Appearance |
|---|---|---|---|---|
| 118 | 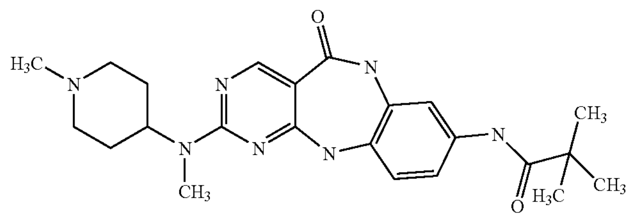 | 3.41 | 437.54 | yellow, solid |
| 119 | 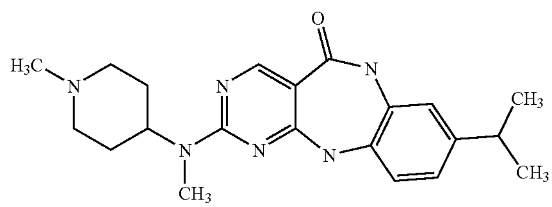 | 3.7 | 380.49 | yellow, solid |
| 120 | 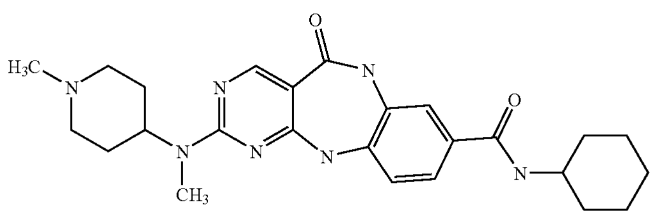 | 3.6 | 463.58 | yellow, solid |
| 121 | 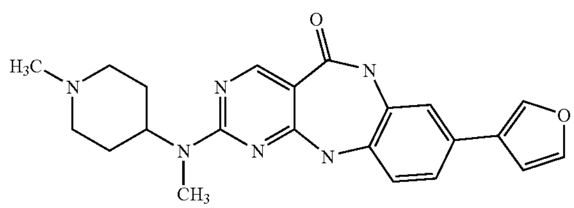 | 3.57 | 404.47 | yellow, solid |
| 122 | 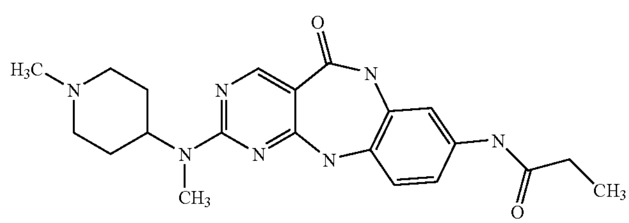 | 2.99 | 409.49 | yellow, solid |
| 123 | 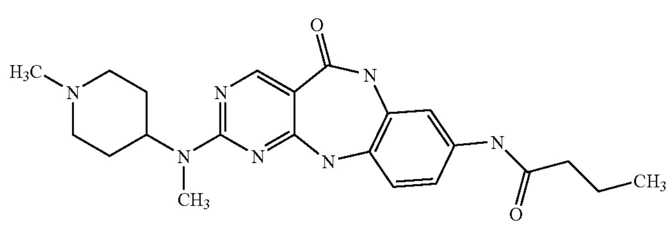 | 3.2 | 423.52 | yellow, solid |
| 124 | 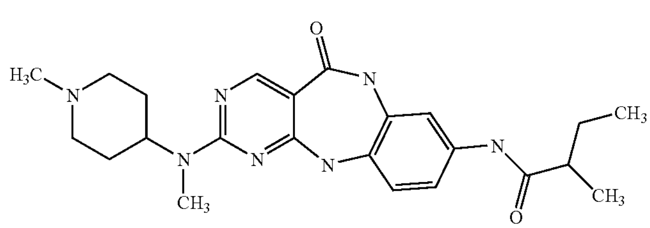 | 3.39 | 437.54 | yellow, solid |

Pharmaceutically or physiologically acceptable derivatives are taken to mean, for example, salts of the compounds according to the invention and also so-called prodrug compounds. Such derivatives are known in the person skilled in the art. A review of physiologically tolerated derivatives is given in Burgers Medicinal Chemistry And Drug Discovery, 5th Edition, Vol. 1: Principles and Practice. Prodrug compounds are taken to mean compounds of the formula I which have been modified with, for example, alkyl or acyl groups, sugars or oligopeptides and which are rapidly cleaved or liberated in the organism to give the effective compounds according to the invention. These also include biodegradable polymer derivatives of the compounds according to the invention, as described, for example, in Int. J. Pharm. 115:61-67 (11995).

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates or p-toluenesulfonates.

solvates of the compounds of the formula I are taken to mean adductions of inert solvent molecules onto the compounds of the formula I which form owing to their mutual attractive force. solvates are, for example, hydrates, such as monohydrates or dihydrates, or alcoholates, i.e. addition compounds with alcohols, such as, for example, with methanol or ethanol.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or prevention of side effects or also reduction in the progress of a disease, condition or disorder. The term "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The present invention furthermore relates to a process for the preparation of compounds of the formula I and physiologically acceptable salts, derivatives, solvates and stereoisomers thereof, characterised in that, in a first step, a compound of the formula VIII

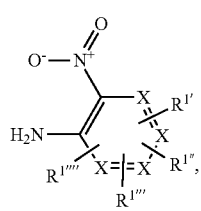

VIII in which all radicals have the meaning indicated above, is reacted with a compound of the formula VII

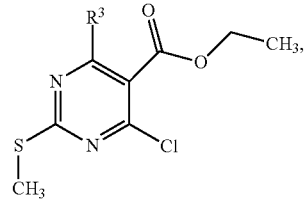

VII in which all radicals have the meanings indicated above, to give a compound of the formula VI

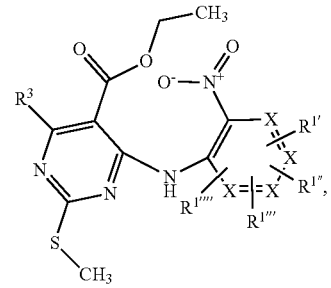

VI which is reduced to a compound of the formula V

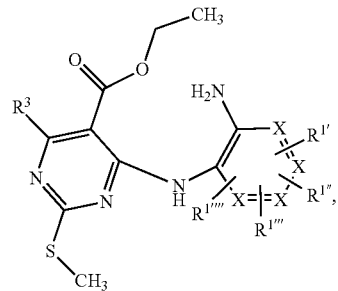

V which is then saponified in the next step to a compound of the formula IV

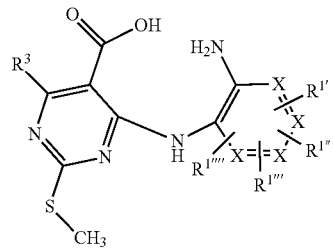

IV which is cyclised further to a diazepinone of the formula III

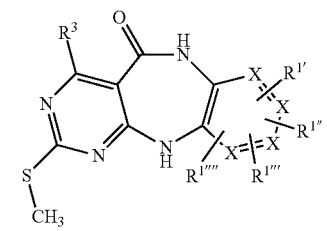

III which, after an increase in the reactivity of the thioether, for example by oxidation to a sulfone, is substituted by a compound of the formula II

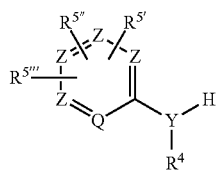

giving a compound of the formula Ib

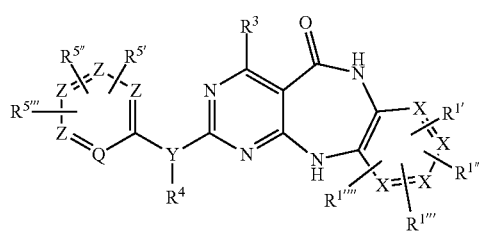

which is finally, if the radicals R$^{2'}$, R$^{2''}$ have a meaning other than H, converted into a compound of the formula I

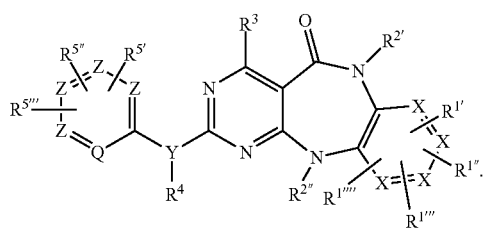

The compounds of the formula VIII, VII and II are generally known. If they are novel, they can be prepared by methods known per se, as described in the literature (for example in standard works, such as Houben-Weyl, Methoden der organischen Chemie [Methods of Organic Chemistry], Georg Thieme Verlag, Stuttgart; Organic Reactions, John Wiley & Sons, Inc., New York).

The compounds of the formula I and also the starting materials for their preparation are prepared by methods known per Se, as described in the literature (for example in standard works, such as Houben-Weyl, Methoden der organischen Chemie [Methods of Organic Chemistry], Georg Thieme Verlag, Stuttgart; Organic Reactions, John Wiley & Sons, Inc., New York), to be precise under reaction conditions as are known and suitable for the said reactions. Use can also be made here of variants known per se which are not mentioned here in greater detail.

The diazepinones of the formula I can preferably be obtained by proceeding as follows:

a) A compound of the formula VIII is added to a compound of the formula VIII, optionally working without a solvent or in an inert solvent, and the reaction mixture is stirred at elevated temperature. When the reaction is complete, the compound of the formula VI is isolated from the reaction mixture by chromatography or after precipitation as a solid, preferably crystalline.

b) The product from (a) is hydrogenated to give a compound of the formula V at room temperature and atmospheric pressure by means of a suitable catalyst, c) The reaction product from step (b) is saponified at elevated temperature, and the resultant compound of the formula IV is purified and separated off from the reaction mixture.

d) The product from (c) is then cyclised with the aid of suitable coupling reagents to give a compound of the formula III and purified.

e) The thioether obtained in step (d) is subsequently, in order to increase the reactivity, treated with an agent such as meta-chloroperbenzoic acid in THF, dichloromethane, methyl iodide in acetonitrile or chlorine in THF.

f) Finally, the compound of the formula III pretreated in this way is nucleophilically substituted by a compound of the formula II, giving a compound of the formula I, which is purified—for example by chromatography.

The reactions described above are generally carried out in an inert solvent. Suitable inert solvents for the reactions described above are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, N-methylpyrrolidone (NMP), dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Preference is given to sulfoxides, such as dimethyl sulfoxide (DMSO).

The amount of solvent is not crucial, 5 g to 500 g of solvent can preferably be added per g of the product to be formed.

In general, the process is carried out at a pressure of 1 to 200 bar, but preferably at atmospheric pressure.

Depending on the conditions used, the reaction temperature for the reactions described above is between about −10 and 200° C., normally between −5 and 100° C., preferably between 0 and 80° C.

Depending on the conditions used, the reaction time is between a few 15 minutes and a number of days, preferably in the region of a number of hours.

The reaction can also be carried out in the heterogeneous phase, in which case use is preferably made of an aqueous phase and a benzene or toluene phase, a solid phase and a dichloromethane or chloroform phase and a THF phase. Use is made here of a phase-transfer catalyst, such as, for example, tetrabutylammonium iodide, and optionally an acylation catalyst, such as, for example, dimethylaminopyridine.

A base of the formula I obtained can be converted into the associated acid-addition salt using an acid. Suitable for this reaction are acids which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid, sulfamic acid, furthermore organic acids, in detail aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid; benzenesulfonic acid, p-toluenesulfonic acid, naphthalenemono- and -disulfonic acids, laurylsulfuric acid.

If desired, the free bases of the formula I can be liberated from their salts by treatment with strong bases, such as sodium hydroxide, potassium hydroxide, sodium carbonate or potassium carbonate, so long as no other acidic groups are present in the molecule.

Compounds of the formula I can furthermore be obtained by liberating them from one of their functional derivatives by treatment with a solvolysing or hydrogenolysing agent.

Preferred starting materials for the solvolysis or hydrogenolysis are those which otherwise conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group and/or those which carry a hydroxyl-protecting group instead of the H atom of a hydroxyl group, for example those which conform to the formula I, but carry a —COOR" group, in which R" denotes a hydroxyl-protecting group, instead of a —COOK group.

Preferred starting materials are also the oxadiazole derivatives, which can be converted into the corresponding amidino compounds.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxyalkanoyl, such as PGA; alkoxycarbonyl, such as methoxycarbonyl, ethoxycarbonyl, 2,2,2-trichloroethoxycarbonyl, BOG (tert-butoxycarbonyl), 2-iodoethoxycarbonyl; aralkoxycarbonyl, such as CBZ ("carbobenzoxy"), 4-methoxybenzyloxycarbonyl, FMOC; arylsulfonyl, such as Mtr. Preferred amino-protecting groups are BOC and Mtr, furthermore CBZ, Fmoc, benzyl and acetyl.

Furthermore, free amino groups can be acylated in a conventional manner using an acid chloride or anhydride or alkylated using an unsubstituted or substituted alkyl halide, or reacted with CH3-C(=NH)—OEt, advantageously in an inert solvent, such as dichloromethane or THF, and/or in the presence of a base, such as triethylamine or pyridine, at temperatures between –60 and +30° C.

The expression "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl or silyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature, RT).

The BOC, OBut and Mtr groups can, for example, preferably be cleaved off using TFA in dichloromethane or using approximately 3 to 5N HCl in dioxane at 15-30° C., the FMOC group can be cleaved off using an approximately 5 to 50% solution of dimethylamine, diethylamine or piperidine in DMF at 15-30° C.

Hydrogenolytically removable protecting groups (for example CBZ, benzyl or the liberation of the amidino group from its oxadiazole derivative) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Esters can be saponified, for example, using acetic acid or using NaOH or KOH in water, water/THF or water/dioxane, at temperatures between 0 and 100° C.

Further methods for the removal of protecting groups is described, for example, in Theodora W. Green, Peter G. M. Wuts: Protective Groups in Organic Synthesis, 3rd Edition John Wiley & Sons (1999).

Compounds of the formula I according to the invention may be chiral owing to their molecular structure and accordingly occur in various enantiomeric forms. They can therefore exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical, biochemical or physical measures known to the person skilled in the art or even employed as such in the synthesis.

After removal of the solvent, the compounds of the formula I can be obtained by conventional work-up steps, such as, for example, addition of water to the reaction mixture and extraction. It may be advantageous subsequently to carry out a distillation or crystallisation for further purification of the product.

The invention furthermore relates to medicaments comprising at least one compound according to the invention and/or physiologically acceptable salts, derivatives, solvates and stereoisomers thereof, including mixtures thereof in all ratios.

A pharmaceutical composition according to the invention may furthermore comprise further excipients and/or adjuvants and optionally one or more further medicament active ingredients.

The invention furthermore relates to a process for the preparation of a medicament, characterised in that a compound according to the invention and/or one of its physiologically acceptable salts, derivatives, solvates and stereoisomers, including mixtures thereof in all ratios, is brought into a suitable dosage form together with a solid, liquid or semi-liquid excipient or adjuvant.

The invention also relates to a set (kit) consisting of separate packs of
a) an effective amount of a compound according to the invention and/or physiologically acceptable salts, derivatives, solvates and stereoisomers thereof, including mixtures thereof in all ratios, and
b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Medicaments can be administered in the form of dosage units which comprise a predetermined amount of active ingredient per dosage unit. Such a unit can comprise, for example, 0.5 mg to 1 g, preferably 1 mg to 700 mg, particularly preferably 5 my to 100 mg, of a compound according to the invention, depending on the condition treated, the method of administration and the age, sex, weight and condition of the patient. Preferred dosage unit formulations are those which comprise a daily dose or part-dose, as indicated above, or a corresponding fraction thereof of an active ingredient. Furthermore, medicaments of this type can be prepared using a process which is generally known in the pharmaceutical art.

Medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such medicaments can be prepared using all processes known in the pharmaceutical art by, for example, combining the active ingredient with the excipient(s) or adjuvant(s).

Medicaments adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a nontoxic alcoholic vehicle. Suspensions can be formulated by dispersion of the compound in a nontoxic vehicle. Solubilisers and emulsifiers, such as, for example, ethoxylated isostearyl alcohols and polyoxyethylene sorbitol ethers, preservatives, flavour additives, such as, for example, peppermint oil, or natural sweeteners or saccharin or other artificial sweeteners, and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Medicaments adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6):318 (1986).

Medicaments adapted for topical administration can be formulated as ointments, creams, suspensions, lotions, powders, solutions, pastes, gets, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base Medicaments adapted for topical application to the eye include eye drops, in which the active ingredient is dissolved or suspended in a suitable carrier, in particular an aqueous solvent.

Medicaments adapted for topical application in the mouth encompass lozenges, pastilles and mouthwashes.

Medicaments adapted for rectal administration can be administered in the form of suppositories or enemas.

Medicaments adapted for nasal administration in which the carrier sub-stance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Medicaments adapted for administration by inhalation encompass finely particulate dusts or mists, which can be generated by various types of pressurised dispensers with aerosols, nebulisers or insufflators.

Medicaments adapted for vaginal administration can be administered as pessaries, tampons, creams, gels, pastes, foams or spray formulations.

Medicaments adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and nonaqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the medicaments according to the invention may also comprise other agents usual in the art with respect to the particular type of pharmaceutical formulation; thus, for example, medicaments which are suitable for oral administration may comprise flavours.

A therapeutically effective amount of a compound of the present invention depends on a number of factors, including, for example, the age and weight of the recipient, the precise condition that requires treatment, and its severity, the nature of the formulation and the method of administration, and is ultimately determined by the treating doctor or vet. However, an effective amount of a compound of the formula I for the treatment of the diseases according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as a fraction of the effective amount of the compound according to the invention per se.

The compounds according to the invention exhibit an advantageous biological activity which can easily be detected in enzyme assays. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The present invention relates to compounds according to the invention as effectors, preferably as inhibitors of the signalling pathways described here. The invention therefore particularly preferably relates to compounds according to the invention as activators and inhibitors of protein kinases, preferably as inhibitors of serine/threonine kinases, in particular of phosphoinositide-dependent kinase (PDK). The compounds according to the invention are particularly effective here in the inhibition of serine/threonine kinase PDK1.

As discussed above, the signalling pathways influenced by the compounds according to the invention are relevant for various diseases. Accordingly, the compounds according to the invention are useful in the prophylaxis and/or treatment of diseases which are dependent on the said signalling pathways through interaction with one or more of the said signalling pathways.

The present invention therefore furthermore relates to the use of compounds according to the invention and/or physiologically acceptable salts, derivatives, solvates and stereoisomers thereof, including mixtures thereof in all ratios, for the preparation of a medicament for the treatment and/or prophylaxis of diseases, in particular diseases that are caused, mediated and/or propagated by protein kinases and/or by kinase-mediated signal transduction. Preference is given here to serine/threonine kinases, particularly preferably PDK1.

In addition, the present compounds are suitable as pharmaceutical active ingredients for mammals, in particular for humans, in the treatment of kinase-induced diseases. The expression "kinase-induced diseases" refers to pathological conditions which are dependent on the activity of one or more protein kinases. Protein kinases participate either directly or indirectly in the signal transduction pathways of a variety of cellular activities, including proliferation, adhesion and migration, as well as differentiation. Diseases associated with protein kinase activity include cancers tumour growth, arteriosclerosis, diabetic retinopathy and inflammatory diseases.

The diseases discussed here are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative diseases.

In this connection, brain cancer, lung cancer, squamous cell cancer, bladder cancer, gastric cancer, pancreatic cancer, hepatic cancer, renal cancer, intestinal cancer, breast cancer, head cancer, neck cancer, oesophageal cancer, gynaecological cancer, thyroid cancer, lymphomas, chronic leukaemia and acute leukaemia are to be regarded as cancerous diseases, all of which are usually counted in the group of hyperproliferative diseases. Especially cancerous cell growth and especially cancerous cell growth mediated directly or indirectly by PDK1 is a disease which is a target of the present invention.

The present invention therefore relates to the use of compounds according to the invention for the preparation of a medicament for the treatment and/or prophylaxis of the said diseases and also to a method for the treatment of the said diseases which comprises the administration of one or more compounds according to the invention to a patient in need of such an administration.

The recipient or patient can belong to any mammalian species, for example a primate species, particularly humans; rodents, including mice, rats and hamsters; rabbits; horses, cows, dogs, cats, etc. Animal models are of interest for experimental investigations, providing a model for the treatment of human disease.

The responsiveness of a particular cell to treatment with the compounds according to the invention can be determined by in-vitro tests. Typically, a culture of the cell is incubated with a compound according to the invention at various concentrations for a periodine of time which is sufficient to allow the active ingredients to induce cell death or to inhibit migration, usually between about one hour and one week. In-vitro tests can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the specific cell count, and may be continued until essentially no more undesired cells are detected in the body.

For the identification of kinase inhibitors, various assay systems are available. In scintillation proximity assay (Sorg et al., J. of. Biomolecular Screening:7, 11-19, 2002) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 191-214, 2002).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al., Biochem. J. 366: 977-981, 2002).

There are many diseases and conditions associated with deregulation of cell proliferation and cell death (apoptosis). The diseases and conditions that can be treated, prevented or ameliorated by compounds according to the invention include, but are not limited to, the diseases and conditions listed below. The compounds according to the invention are suitable in the treatment and/or prophylaxis of a number of different diseases and conditions where there is proliferation and/or migration of smooth muscle cells and/or inflammatory cells into the intimal layer of a vessel, resulting in restricted blood flow through that vessel, for example in the case of neointimal occlusive lesions. Occlusive transplant vascular diseases of interest include atherosclerosis, coronary vascular disease after transplantation, vein graft stenosis, peri-anastomotic prosthetic restenosis, restenosis after angioplasty or stent placement and the like.

The present invention encompasses the use of the compounds according to the invention for the treatment or prevention of cancer. In particular, the invention relates to the use of compounds according to the invention and/or physiologically acceptable salts, derivatives, solvates and stereoisomers thereof, including mixtures thereof in all ratios, for the preparation of a medicament for the treatment and/or prophylaxis of solid tumours, where the solid tumour is particularly preferably selected from the group consisting of brain tumour, tumour of the urogenital tract, tumour of the lymphatic system, stomach tumour, laryngeal tumour, lung tumour. Solid tumours selected from the group consisting of monocytic leukaemia, lung adenocarcinoma, small-cell and non-small-cell lung carcinomas, renal cell carcinoma, endometrial carcinoma, multiple myeloma, prostate cancer, colorectal cancer, pancreatic cancer, glioblastomas and breast carcinoma can preferably also be treated with medicaments comprising compounds according to the invention.

The present compounds are also suitable for combination with known anti-cancer agents. These known anti-cancer agents include the following: oestrogen receptor modulators, androgen receptor modulators, retinoid receptor modulators, cytotoxic substances, antiproliferative agents, prenyl-protein transferase inhibitors, HMG-CoA reductase inhibitors, HIV protease inhibitors, reverse transcriptase inhibitors, growth factor inhibitors and angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic substances" refers to compounds which result in cell death primarily through direct action on the cellular function or which inhibit or interfere with cell mitosis, including alkylating agents, tumour necrosis factors, intercalators, microtubulin inhibitors and topoisomerase inhibitors. Examples of cytotoxic substances include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu[diamine-platinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN 10755 and 4-demethoxy-3-deamino-3-aziridinyl-4-methylsulfonyldaunorubictn (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS114476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]-acridin-6-one, N-[1-[2-(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno-[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal anti-bodies to growth factors, such as erbitux, trastuzumab, and tumour suppressor genes, such as p53, which can be delivered via recombinant virus-mediated gene transfer (see U.S. Pat. No. 6,069,134, for example).

WORKING EXAMPLES

The following examples serve to illustrate the invention. The invention is not restricted to the examples. On the other hand, information from the examples, in particular on the reaction conditions, can generally be applied for the purposes of the invention beyond the specific circumstances described.

Example 1

Preparation of Compounds of the Formula I

The following procedure is followed in accordance with the diagram below:
1.1. A mixture of nitroaniline 1a (1 equivalent) is reacted with 2 (2 equivalents) for 10 minutes at 130° C. without a solvent. 3a is precipitated from the resultant crude product by addition of ethyl acetate:

Ethyl 4-(4-methoxy-2-nitrophenylamino)-2-methylsulfanylpyrimidine-5-carboxylate, 387 mg (43%); yellowish powder; HPLC: 2.73 min; LC-MS: 2.023, 365.0 m/e.

The following compounds of the formula VI can be obtained analogously:

3b) Ethyl 4-(4,5-dimethyl-2-nitrophenylamino)-2-methylsulfanylpyrimidine-5-carboxylate: 335 mg (48%); yellowish powder; HPLC: 2.95 min; LC-MS: 2.27 min, 363.0 m/e.

3c) Ethyl 4-(4-methyl-2-nitrophenylamino)-2-methylsulfanylpyrimidine-5-carboxylate: 426 mg (49%); yellowish powder; HPLC: 2.85 min; LC-MS: 2.170 min, 349.0 m/e.

3d) Ethyl 4-(4-chloro-2-nitrophenylamino)-2-methylsulfanylpyrimidine-5-carboxylate: 1585 mg (72%); yellowish powder; HPLC: 2.95 min; LC-MS: 2.606 min, 369.0 m/e.

3e) Ethyl 4-(5-methyl-2-nitrophenylamino)-2-methylsulfanylpyrimidine-5-carboxylate: 784 mg (75%); yellowish powder; HPLC: 3.03 nm; LC-MS: 2.652 min, 349.0 m/e.

3f) Ethyl 4-(4-methoxy-2-nitrophenylamino)-2-methylsulfanylpyrimidine-5-carboxylate: 387 mg (43%); yellowish powder; HPLC: 2.73 min; LC-MS: 2.023 min, 365.0 m/e.

3g) Ethyl 4-(4-ethoxy-2-nitrophenylamino)-2-methylsulfanylpyrimidine-5-carboxylate 3h) Ethyl 2-methylsulfanyl-4-(3-nitropyridin-2-ylamino)pyrimidine-5-carboxylate 3i) Ethyl 4-(4-bromo-2-nitrophenylamino)-2-methylsulfanylpyrimidine-5-carboxylate 3j) Ethyl 2-methylsulfanyl-4-(4-methyl-3-nitropyridin-2-ylamino)pyrimidine-5-carboxylate 1.2 3a is dissolved in THF and reduced to 4a over 24 h at room temperature and atmospheric pressure with the aid of Pd/C as catalyst and hydrogen. The catalyst is filtered off, rinsed with THF, and the desired product is obtained by removal of the solvent by distillation in vacuo:

ethyl 4-(2-amino-4-methoxyphenylamino)-2-methylsulfanylpyrimidine-5-carboxylate: 874 mg (100%); yellow powder; HPLC: 2.27 min; LC-MS: 1.38 min, 335.0 m/e.

The following compounds of the formula V can be obtained analogously:

4b) Ethyl 4-(2-amino-4,5-dimethylphenylamino)-2-methylsulfanylpyrimidine-5-carboxylate: 640 mg (100%); yellow powder; HPLC: 2.28 min; LC-MS: 1.373 min, 333.0 m/e.

4c) Ethyl 4-(2-amino-4-methylphenylamino)-2-methylsulfanylpyrimidine-5-carboxylate: 686 mg (93%); yellow powder; HPLC: 2.27 min; LC-MS: 1.41 min, 319.0 m/e.

4d) Ethyl 4-(2-amino-4-chlorophenylamino)-2-methylsulfanylpyrimidine-5-carboxylate: 770 mg (97%); yellow powder; HPLC: 2.51 min; LC-MS: 2.79 min, 339.0 m/e.

4e) Ethyl 4-(2-amino-5-methylphenylamino)-2-methylsulfanylpyrimidine-5-carboxylate: 771 mg (98%); yellow powder; HPLC: 2.23 min; LC-MS: 1.29 min, 319.0 m/e.

4f) Ethyl 4-(2-amino-4-methoxyphenylamino)-2-methylsulfanylpyrimidine-5-carboxylate: 874 mg (100%); yellow powder; HPLC: 2.27 min; LC-MS: 1.38 min, 335.0 m/e.

4g) Ethyl 4-(2-amino-4-ethoxyphenylamino)-2-methylsulfanylpyrimidine-5-carboxylate 4h) Ethyl 4-(3-aminopyridin-2-ylamino)-2-methylsulfanylpyrimidine-5-carboxylate 4i) Ethyl 4-(2-amino-4-bromophenylamino)-2-methylsulfanylpyrimidine-5-carboxylate 1.3 4a is saponified without further purification at 100° C. (30 min) in a microwave oven using 1.5 equivalents of sodium hydroxide solution in dioxane (10 ml/9). The desired product (5a) is precipitated by addition of hydrochloric acid, filtered off with suction, rinsed with a little water and dried:

4-(2-Amino-4-methoxyphenylamino)-2-methylsulfanylpyrimidine-5-carboxylic acid, 450 mg (98%); off-white powder; HPLC: 2.08 min; LC-MS: 0.814 min, 307.0 m/e.

The following compounds of the formula IV can be obtained analogously:

5b) 4-(2-Amino-4,5-dimethylphenylamino)-2-methylsulfanylpyrimidine-5-carboxylic acid: 911 mg (98%); off-white powder; HPLC: 2.12 min; LC-MS: 1.523 min, 305.0 m/e.

5c) 4-(2-Amino-4-methylphenylamino)-2-methylsulfanylpyrimidine-5-carboxylic acid: 625 mg (92%); off-white powder; HPLC: 2.09 min; LC-MS: 1.440 min, 291.0 m/e.

5d) 4-(2-Amino-4-chlorophenylamino)-2-methylsulfanylpyrimidine-5-carboxylic acid: 591 mg (84%); off-white powder; HPLC: 2.31 min; LC-MS: 1.27 nm, 311.0 m/e.

5e) 4-(2-Amino-5-methylphenylamino)-2-methylsulfanylpyrimidine-5-carboxylic acid: 619 mg (100%); off-white powder; HPLC: 2.07 min; LC-MS: 0.796 min, 291.0 m/e.

5f) 4-(2-Amino-4-methoxyphenylamino)-2-methylsulfanylpyrimidine-5-carboxylic acid: 450 mg (98%); off-white powder; HPLC: 2.08 min; LC-MS: 0.814 min, 307.0 m/e.

5g) 4-(2-Amino-4-ethoxyphenylamino)-2-methylsulfanylpyrimidine-5-carboxylic acid 5h) 4-(3-Aminopyridin-2-ylamino)-2-methylsulfanylpyrimidine-5-carboxylic acid 5i) 4-(2-Amino-4-bromophenylamino)-2-methylsulfanylpyrimidine-5-carboxylic acid 1.4 5a is cyclised with the aid of 1.2 equivalents of N-(3-dimethylaminopropyl)-N'-ethylcarbodiimide hydrochloride, 1.2 equivalents of HOBt and 2.2 equivalents of 4-methylmorpholine to give 6a, and the desired product is extracted with ethyl acetate/nbutanol and purified by column chromatography using a Flash-Master II (see below):

8-methoxy-3-methylsulfanyl-5,10-dihydro-2,4,5,10-tetraazadibenzo[a,d]-cyclohepten-11-one: 263 mg (56%); yellow powder; HPLC: 2.21 min; LC-MS: 1.01 min, 289.0 m/e.

The following compounds of the formula III can be obtained analogously:

6b) 7,8-Dimethyl-3-methylsulfanyl-5,10-dihydro-2,4,5,10-tetraazadibenzo-[a,d]cyclohepten-11-one: 800 mg (93%); yellow powder; HPLC: 2.31 min; LC-MS: 1.769 min, 287.0 m/e.

6c) 8-Methyl-3-methylsulfanyl-5,10-dihydro-2,4,5,10-tetraazadibenzo-[a,d]cyclohepten-11-one: 311 mg (72%); yellow powder; HPLC: 2.24 min; LC-MS: 1.158 min, 273.0 m/e.

6d) 8-Chloro-3-methylsulfanyl-5,10-dihydro-2,4,5,10-tetraazadibenzo-[a,d]cyclohepten-11-one: 108 mg (20%); yellow powder; HPLC: 2.38 min; LC-MS: 1.33 min, 293.0 m/e.

6e) 7-Methyl-3-methylsulfanyl-5,10-dihydro-2,4,5,10-tetraazadibenzo-[a,d]cyclohepten-11-one: 617 mg (94%); yellow powder; HPLC: 2.25 min; LC-MS: 1.189 min, 273.0 m/e.

6f) 8-Methoxy-3-methylsulfanyl-5,10-dihydro-2,4,5,10-tetraazadibenzo[a,d]cyclohepten-1-one: 263 mg (56%); yellow powder; HPLC: 2.21 min; LC-MS: 1.01 min, 289.0 m/e.

6g) 8-Ethoxy-3-methylsulfanyl-5,10-dihydro-2,4,5,10-tetraazadibenzo[a,d]-cyclohepten-11-one 6h) 3-Methylsulfanyl-5,10-dihydro-2,4,5,6,10-pentaazadibenzo[a,d]cyclohepten-1-one 6i) 8-Bromo-3-methylsulfanyl-5,10-dihydro-2,4,5,10-tetraazadibenzo[a,d]cyclohepten-11-one 1.5 For preparation for the substitution, 6a is treated with 4 equivalents of meta-chloroperbenzoic acid in a THF/dichloromethane mixture (ratio 1:1) (15 min 0° C., 2 h RT). After addition of 20% sodium sulfite solution, a precipitate is obtained, which is filtered off with suction and rinsed with a little water. This precipitate comprises about 58% (according to HPLC) of the oxidation product 7a. The precipitate is heated, without further purification, at 100° C. for 30 minutes with 1.2 equivalents of methyl(1-methylpiperidin-4-yl) amine A with addition of 0.1 equivalent of potassium iodide and 1.5 equivalents of potassium carbonate. After filtration and concentration in vacuo, the desired product 8a can be purified by column chromatography by means of preparative HPLC:

8-methoxy-3-(1-methylpiperidin-4-ylamino)-5,10-dihydro-2,4,5,10-tetraazadibenzo[a,d]cyclohepten-11-one: 23 mg (100%); orange-brown solid; HPLC: 2.01 min; LC-MS: 0.458 min, 355.2 m/e.

The following intermediates can be obtained analogously:

5b) 7,8-Dimethyl-3-[methyl(1-methylpiperidin-4-yl) amino]-5,10-dihydro-2,4,5,10-tetraazadibenzo[a,d]cyclohepten-11-one: 11 mg (3% of theory); orange-brown solid; HPLC: 2.06 min; LC-MS: 1.387 min, 367.2 m/e, 8c) 8-Chloro-3-[methyl(1-methylpiperidin-4-yl)amino]-5,10-dihydro-2,4,5,10-tetraazadibenzo[a,d]cyclohepten-11-one: 58 mg (47% of theory); orange-brown solid; HPLC: 2.08 min; LC-MS: 0.678 min, 373.0 m/e.

5d) S-Methoxy-3-[methyl(1-methylpiperidin-4-yl)amino]-5,10-dihydro-2,4,5,10-tetraazadibenzo[a,d]cyclohepten-11-one: 31 mg (9% of theory); orange-brown solid; HPLC, 2.01 min; LC-MS: 1.229 min, 369.2 m/e.

8e) 8-Methyl-3-[methyl(1-methylpiperidin-4-yl)amino]-5,10-dihydro-2,4,5,10-tetraazadibenzo[a,d]cyclohepten-11-one: 20 mg (5% of theory); orange-brown solid; HPLC: 2.02 min; LC-MS: 1.275 min, 353.2 m/e.

8f) 8-Methoxy-3-(1-methylpiperidin-4-ylamino)-5,10-dihydro-2,4,5,10-tetraazadibenzo[a,d]cyclohepten-11-one: 23 mg (100% of theory); orange-brown solid; HPLC: 2.01 min; LC-MS: 0.458 min, 355.2 m/e.

8g) 7-Methyl-3-[methyl(1-methylpiperidin-4-yl)amino]-5,10-dihydro-2,4,5,10-tetraazadibenzo[a,d]cyclohepten-11-one: 13 mg (9% of theory); orange-brown solid; HPLC: 1.92 min; LC-MS: 1.273 min, 353.2 m/e.

8h) 7-Methyl-3-(1-methylpiperidin-4-ylamino)-5,10-dihydro-2,4,56,10-tetraazadibenzo[a,d]cyclohepten-11-one: 5 mg (2% of theory); orange-brown solid; HPLC: 1.96 min; LC-MS: 1.253 min, 339.2 m/e.

8i) 7,8-Dimethyl-3-(1-methylpiperidin-4-ylamino)-5,10-dihydro-2,4,5,10-tetraazadibenzo[a,d]cyclohepten-11-one: 70 mg (21% of theory); orange-brown solid; HPLC: 1.96 min; LC-MS: 1.338 min, 353.2 m/e.

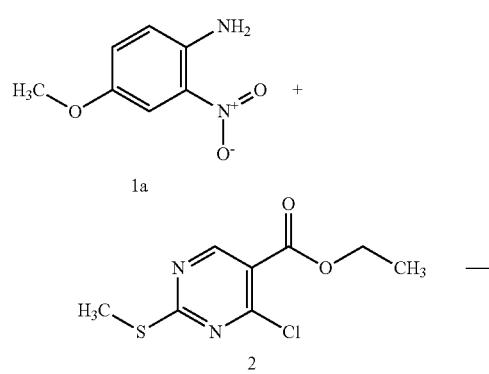

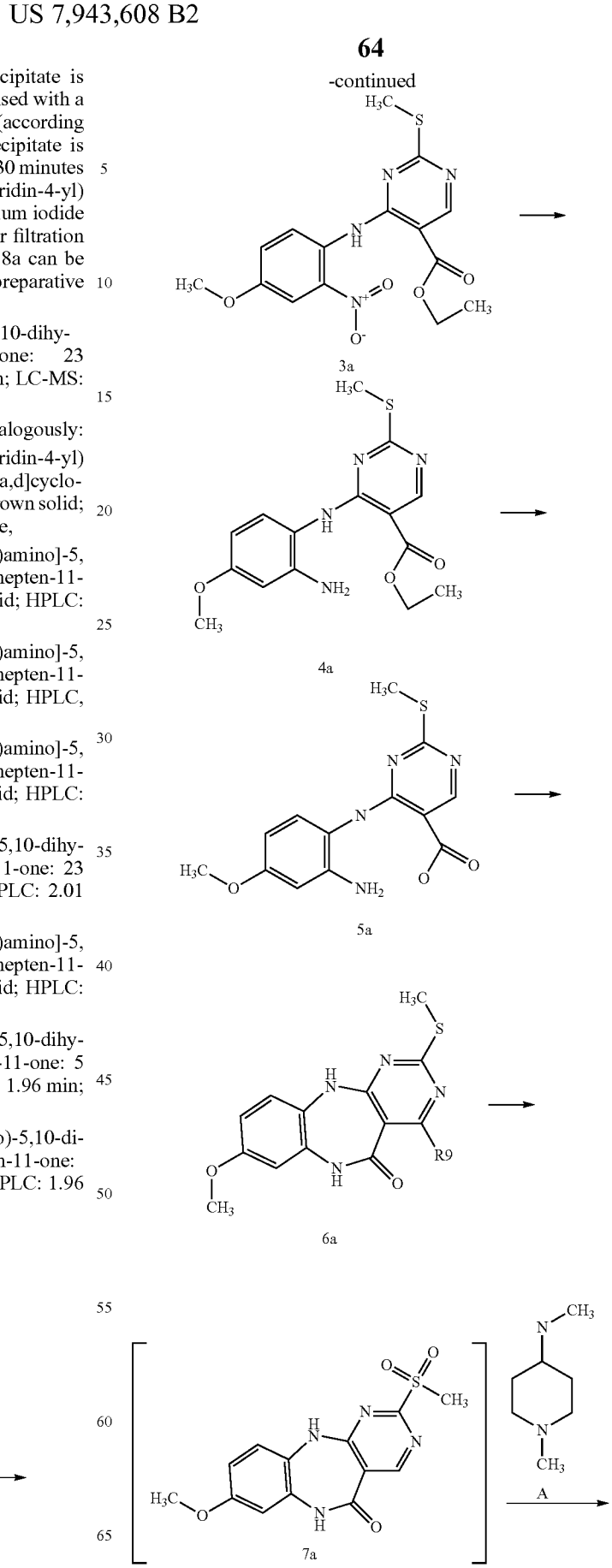

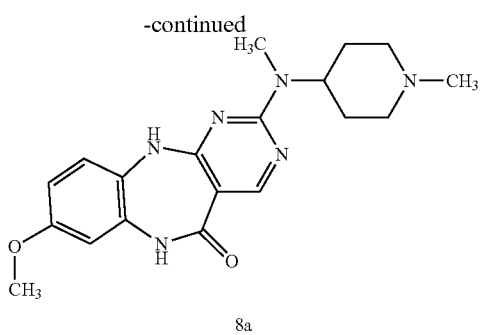

8a

The following equipment is used:

The column chromatography is carried out using the FlashMaster II (Biotage, Sweden). The plastic cartridges are filled with silica gel having a particle size of 0.003-0.006 mm (Merck Eurolab, Darmstadt).

The preparative HPLC is carried out using a Chromolith Prep (RP-18e 100-25 mm) column, a K-1800 gradient pump and a Büchi B684 fraction collector. For the separation, a mixture of water/0.1% of TEA (eluent A) and acetonitrile/0.1% of TEA (eluent B) is employed at a flow rate of 30 ml/min.

Analytical HPLC: the HPLC spectra are recorded and processed using a Lichrograph L-6200A gradient pump, an L-4500A diode array detector and a Chromolith Speed ROD RP-18e 50-4.6 mm column (all Merck, Darmstadt) and with the aid of the D-6500 DAD System Manager Revision 1 computer program. The HPLC purities are measured by means of UV detection at 220 nm. For the purity determinations, a gradient of water/0.1% of TEA (eluent A) and acetonitrile/0.1% of TEA (eluent B) is used at a flow rate of 3 ml/min and a run time of 5 min. The HPLC data denoted by (1) in Table 1 were obtained using this method. For the HPLC data denoted by (2), a flow rate of 1.5 ml/min and a run time of 6 min was used. The retention times determined twice, denoted by an asterisk, indicate the presence of conformers.

The HPLC-MS spectra are recorded and measured using the Agilent system 1100 and a Chromolith Speed ROD RP-18e 50-4.6 mm column. For the separations, a gradient of water/0.1% of TFA (eluent A) and acetonitrile/0.1% of TEA (eluent B) was used at a flow rate of 2.4 ml/min. The HPLC-MS data indicated in Table 1 were obtained using this method.

Example 2

Inhibition of PDK1 ($IC_{50}$)

The kinase assay can be carried out as a 384-well flashplate assay. 3.4 nM His6-PDK1($\Delta$1-50), 400 nM PDKtide (biotin-bA-bA-KTECGTPEYLAPSERREPRILSEEEQE-MEFRDFDYIADWC) and 4 µM ATP (with 0.2 µCi of 33P-ATP/well) are incubated at 3000 for 60 min in a total volume of 50 µl (50 mM TRIS, 10 mM Mg acetate, 0.1% of mercaptoethanol, 0.02% of Brij35, 0.1% of BSA, pH 7.5) with or without test substance (5-10 concentrations). The reaction is stopped using 25 µl of 200 mM EDTA solution, filtered with suction after 30 min at room temperature, and the wells are washed with 3 times 100 µl of 0.9% NaCl solution. The nonspecific content of the kinase reaction (blank) is determined using 100 nM staurosporine. Radioactivity is measured using a Topcount scintillation counter (PerkinElmer, USA). IC50 values are calculated using the RS1 computer program.

Further inhibition constants of compounds according to the invention are shown in Table 1.

The following examples relate to pharmaceutical compositions:

Example 3a

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example 3b

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

Example 3c

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example 3d

Ointment 500 mg of an active ingredient according to the invention are mixed with 99.5 g of Vaseline under aseptic conditions.

Example 3e

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient Example 3f Dragees Tablets are pressed analogously to Example 5e and subsequently coated in a conventional manner with a coating of sucrose, potato starch, talc, tragacanth and dye.

Example 3g

Capsules 2 kg of active ingredient are introduced into hard gelatine capsules in a conventional manner in such a way that each capsule contains 20 mg of the active ingredient.

Example 3h

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

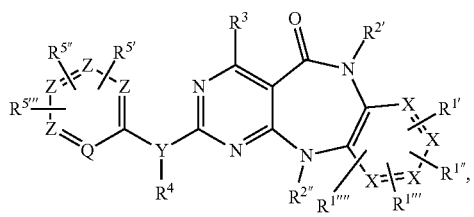

I in which
$R^{1\prime}, R^{1\prime\prime\prime}, R^{1\prime\prime\prime\prime}, R^{1\prime\prime\prime\prime\prime}, R^3, R^4, R^{5\prime}, R^{5\prime\prime\prime}, R^{5\prime\prime\prime\prime}$
each, independently of one another, denote H, A, $R^6$, Ar, $OR^6$, $SR^6$, OAr, SAr, $N(R^6)_2$, NHAr, Hal, $NO_2$, CN, $(CH_2)_m COOR^6$, $(CH_2)_m COOAr$, $(CH_2)_m CON(R^6)_2$, $(CH_2)_m CONAAr$, COA, $COR^6$, COAr, $S(O)_m A$, $S(O)_m Ar$, NACOA, NACOAr, $NASO_2A$, $NASO_2Ar$, NHCOA, NHCOAr, $NHCON(R^6)_2$, NHCONHA, NHCONHAr, $SO_2N(R^6)_2$, $SO_2NAAr$, $M(CH_2)_n N(R^6)_2$, $M(CH_2)_n NAR^6$, $M(CH_2)_n NA_2$, $M(CH_2)_n (R^6)_n$, $M(CH_2)_n (R^6)_n$, $M(CH_2)_n (R^6)_n$, $M(CH_2)_n (R^6)_n$, $M(CH_2)_n$-oxopiperazine, $M(CH_2)_n$-oxomorpholine, $M(CH_2)_n$-oxopyrrolidine, $M(CH_2)_n C(CH_3)_n (CH_2)_n N(R^6)_2$, $M(CH_2)_n M(R^6)_n SO_m A$, $M(CH_2)_n M(R^6)_n SO_m M(R^6)_n$, $M(CH_2)_n M(R^6)_n SO_m Ar$, $(CH_2)_n M(R^6)_n SO_m A$, $(CH_2)_n M(R^6)_n SO_m M(R^6)_n$, $(CH_2)_n M(R^6)_n SO_m Ar$, $M(CH_2)_n SO_m A$, $M(CH_2)_n SO_m N(R^6)_n A$, $M(CH_2)_n SO_m Ar$, $(CH_2)_n SO_m A$, $(CH_2)_n SO_n$, $M(R^6)_n$, $(CH_2)_n SO_m Ar$,
where two adjacent radicals $R^{1\prime}, R^{1\prime\prime\prime}, R^{1\prime\prime\prime\prime}$ or $R^{1\prime\prime\prime\prime\prime}$ may form together a saturated or unsaturated, five- or six-membered carbo- or heterocycle which is optionally mono- or disubstituted by M,
$R^{2\prime}, R^{2\prime\prime}$ each, independently of one another, denote $R^6$,
$R^6$ denotes H, Hal, OH, CN, $NH_2$, $NO_2$, $SO_2$, unbranched or branched alkyl having 1-4 C atoms, in which one $CH_2$ group may be replaced by an O or S atom and/or by an NH, NA, CONH, NHCO or —CH=CH— group and/or, in addition, 1-4H atoms may be replaced by Hal, and in which one $CH_3$ group may be replaced by Hal, OH, CN, $NH_2$, $NHR_7$, $NR^7_2$, $NO_2$ or $SO_2$, where $R^7$=methyl or ethyl, where two radicals $R^6$, together with the atom to which they are linked, may form a saturated or unsaturated five- or six-membered carbo- or heterocycle,
n denotes 0, 1, 2, 3, 4 or 5,
m denotes 0, 1 or 2,
A denotes unbranched, branched or cyclic alkyl having 1-14 C atoms, in which one or two $CH_2$ groups may be replaced by an O or S atom and/or by an NH, CONH, NHCO, CO or —CH=CH— group and/or, in addition, 1-7H atoms may be replaced by Hal, and in which one or two $CH_3$ groups may be replaced by $R^6$,
Ar denotes a mono- or bicyclic aromatic homo- or heterocycle having 1 to 4 N, O and/or S atoms and 5 to 10 skeleton atoms, which may be unsubstituted or mono-, di- or trisubstituted by carbonyl oxygen, Hal, A, OH, OA, $NH_2$, NHA, $NA_2$, $NO_2$, CN, OCN, SCN, COOH, COOA, $CONH_2$, CONHA, $CONA_2$, NHCOA, $NHCONH_2$, $NHSO_2A$, CHO, COA, $SO_2NH_2$ and/or $S(O)_m A$,
Hal denotes F, Cl, Br or I,
X denotes $CR^1$, $CHR^1$, N, $NR^1$, O or S, where at least one X group in each compound of the formula I is $CR^1$ or $CHR^1$ and where furthermore an O or S group is not bonded directly to an N, $NR^1$, O or S group,
Y denotes $NR^4$, O or S,
Z denotes $CR^5$, $CHR^5$, N, $NR^5$, O or S, where at least two Z groups in each compound of the formula I are $CR^5$ or $CHR^5$ and where furthermore an O or S group is not bonded directly to an N, $NR^5$, O or S group,
Q denotes $CR^5$, $CHR^5$, or a bond, and
M denotes NH, O, S,
or a pharmaceutically acceptable salt, solvate, stereoisomer or mixture thereof.

2. The compound according to claim 1, of formula AII

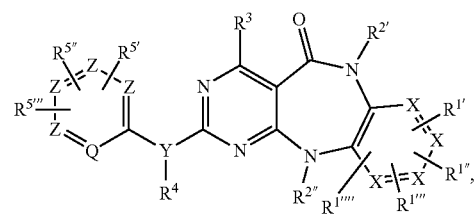

AII in which $R^{1\prime}, R^{1\prime\prime\prime}, R^{1\prime\prime\prime\prime}, R^{1\prime\prime\prime\prime\prime}, R^{2\prime}, R^{2\prime\prime}, R^3, R^4, R^{5\prime}, R^{5\prime\prime\prime}, R^{5\prime\prime\prime\prime}, R^6$, Q, X, Y and Z have the meaning indicated for formula I, or a pharmaceutically acceptable salt, solvate or stereoisomer or mixture thereof.

3. The compound according to claim 1, of formula AIII

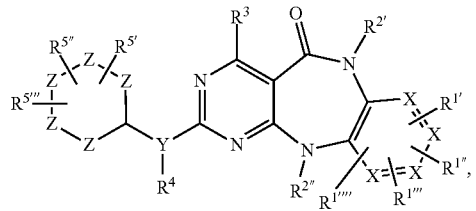

AIII in which $R^{1\prime}, R^{1\prime\prime\prime}, R^{1\prime\prime\prime\prime}, R^{1\prime\prime\prime\prime\prime}, R^{2\prime}, R^{2\prime\prime}, R^3, R^4, R^{5\prime}, R^{5\prime\prime\prime}, R^{5\prime\prime\prime\prime}, R^6$, X, Y and Z have the meaning indicated for formula I, or a pharmaceutically acceptable salt, solvate or stereoisomer or mixture thereof.

4. The compound according to claim 1, of formula AIV

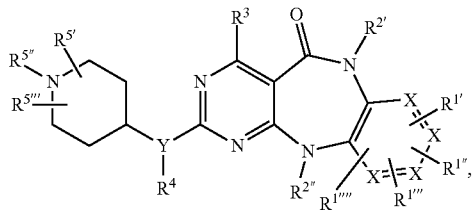

AIV in which $R^{1\prime}$, $R^{1\prime\prime}$, $R^{1\prime\prime\prime}$, $R^{1\prime\prime\prime\prime}$, $R^{2\prime}$, $R^{2\prime\prime}$, $R^3$, $R^4$, $R^{5\prime}$, $R^{5\prime\prime}$, $R^{5\prime\prime\prime}$, $R^6$, X, Y and Z have the meaning indicated for the formula I, or a pharmaceutically acceptable salt, solvate, or stereoisomer or mixtures thereof.

5. The compound according to claim 1, of formula AV

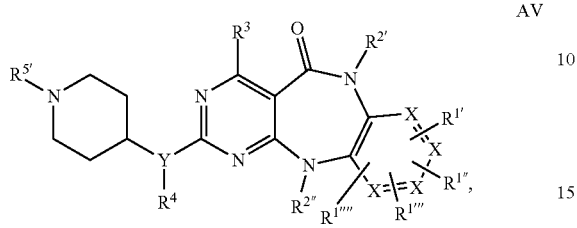

AV in which $R^{1\prime}$, $R^{1\prime\prime\prime}$, $R^{1\prime\prime\prime\prime}$, $R^{2\prime}$, $R^{2\prime\prime}$, $R^3$, $R^4$, $R^{5\prime}$, $R^{5\prime\prime}$, $R^{5\prime\prime\prime}$, $R^6$, X, Y and Z have the meaning indicated for formula I, or a pharmaceutically acceptable salt, solvate or stereoisomer or mixtures thereof.

6. The compound according to claim 1, in which
Aa:
X denotes $CR^1$ or $CHR^1$,
Ab:
one X denotes N or $NR^1$,
the other three X denote $CR^1$ or $CHR^1$,
Ac:
$R^{5\prime}$ denotes methyl,
Ad:
$R^3$ denotes H,
Ae:
$R^{2\prime}$, $R^{2\prime\prime}$ denote H,
Af:
Y denotes $NR^4$,
$R^4$ denotes H or methyl,
Ag:
$R^{1\prime}$, $R^{1\prime\prime}$ denote H,
$R^{1\prime\prime\prime}$ denotes H, Hal or methyl,
$R^{1\prime\prime\prime\prime}$ denotes H, Hal, methyl, ethyl, n-propyl, 2-propyl, butyl, isobutyl, sec-butyl tert-butyl, methoxy, $CHal_3$, $CF_3$, OH, $OCH_2CH_2OH$, $SCH_2CH_3$, $NHCH_3$, $N(CH_3)_2$, CN, COOH, $COOCH_3$, $SO_2OH$, $OCHal_3$, $OCF_3$, NHCOA, NHCOAr, $NHCON(R^6)_2$, NHCONHA, NHCONHAr, where A and $R^6$ are H, cyclopentyl, cyclohexyl, n-propyl, 2-propyl, ethyl, sec-butyl or tert-butyl and Ar is thiophen-2 or 3-yl, 3,5-dimethylisoxazol-4-yl, and two radicals $R^6$, together with the amide nitrogen atom, may form a tetrahydropyrrole ring,
Ah:
one X denotes N or $NR^1$,
the other three X denote $CR^1$ or $CHR^1$,
Y denotes $NR^4$,
$R^4$ denotes H or methyl,
$R^{5\prime}$ denotes methyl,
$R^{2\prime}$, $R^{2\prime\prime}$, $R^3$ denote H,
$R^{1\prime}$, $R^{1\prime\prime}$ denote H,
$R^{1\prime\prime\prime}$ denotes H, Hal or methyl,
$R^{1\prime\prime\prime\prime}$ denotes H, Hal, methyl, ethyl, n-propyl, 2-propyl, butyl, isobutyl, sec-butyl tert-butyl, methoxy, $CHal_3$, $CF_3$, OH, $OCH_2CH_2OH$, $SCH_2CH_3$, $NHCH_3$, $N(CH_3)_2$, CN, COOH, $COOCH_3$, $SO_2OH$, $OCHal_3$, $OCF_3$, NHCOA, NHCOAr, $NHCON(R^6)_2$, NHCONHA, NHCONHAr, where A and $R^6$ are H, cyclopentyl, cyclohexyl, n-propyl, 2-propyl, ethyl, sec-butyl or tert-butyl and Ar is thiophen-2 or 3-yl, 3,5-dimethylisoxazol-4-yl, and two radicals $R^6$, together with the amide nitrogen atom, may form a tetrahydropyrrole ring, or a pharmaceutically acceptable salt, solvate or stereoisomer or mixtures thereof.

7. A process for the preparation of a compound of formula I or a physiologically acceptable salt, solvate or stereoisomer or mixtures thereof, comprising reacting a compound of the formula VIII

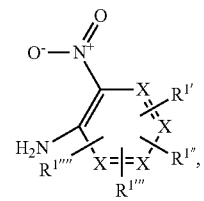

VIII with a compound of formula VII

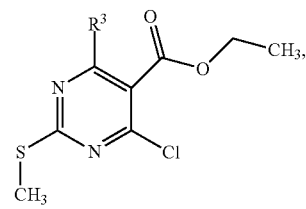

VII to give a compound of formula VI

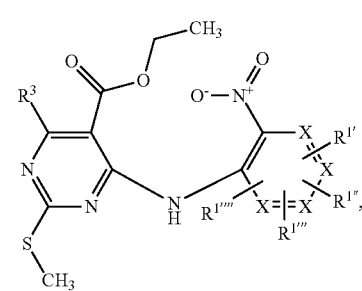

VI reducing to a compound of formula V

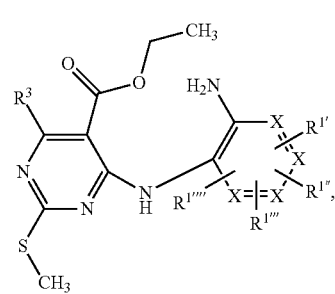

V saponifying to a compound of formula IV

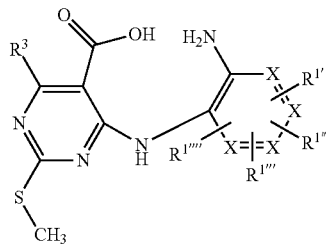

cyclizing to a diazepinone of formula III

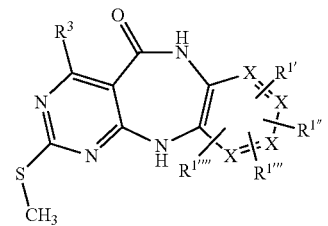

after an increase in the reactivity of the thioether, substituting by a compound of formula II

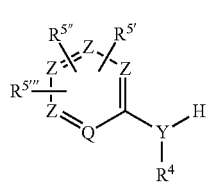

to give a compound of formula Ib

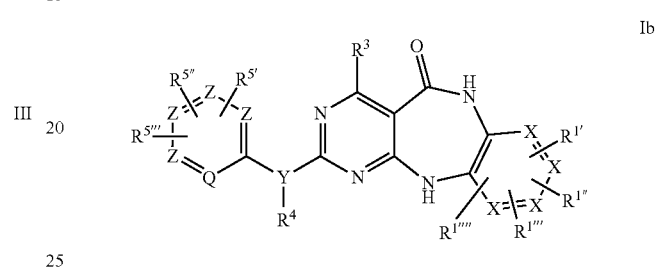

and optionally, if $R^{2'}$, $R^{2''}$ have a meaning other than H, converting into a compound of formula I, or converting a base or acid of formula I into one of its salts.

* * * * *

UNITED STATES PATENT AND TRADEMARK OFFICE
CERTIFICATE OF CORRECTION

PATENT NO. : 7,943,608 B2
APPLICATION NO. : 12/158333
DATED : May 17, 2011
INVENTOR(S) : Melanie Schultz et al.

It is certified that error appears in the above-identified patent and that said Letters Patent is hereby corrected as shown below:

Title page in Section (54) and column 1:
 The Title of the Invention which reads "DIAZEPINOES" should read --DIAZEPINONES--

Column 67, line 42
 reads: "$SO_mA, (CH_2)_nSO_nM(R^6)_n, (CH_2)_nSO_mAr,$"
 should read -- $SO_mA, (CH_2)_nSO_mM(R^6)_n, (CH_2)_nSO_mAr,$ --

Column 69, line 2
 reads: "$R^{5'''}, R^6$, X, Y and Z have the meaning indicated for the"
 should read -- $R^{5'''}, R^6$, X, Y and Z have the meaning indicated for --

Column 69, line 18
 reads " in which R1', R1''', R1'''', R2', R2'', R3, R4, R5', R5'', R5''', R6,"
 should read -- in which R1', R1'', R1''', R1'''', R2', R2'', R3, R4, R5', R5'', R5''', R6,--

Column 69, line 34
 reads "R2, R2 denote H,"
 should read -- R2', R2'' denote H, --

Column 69, line 51
 reads "Ah:"
 should read -- or Ah: --

Signed and Sealed this
Twenty-second Day of November, 2011

David J. Kappos
*Director of the United States Patent and Trademark Office*